Figure 1:
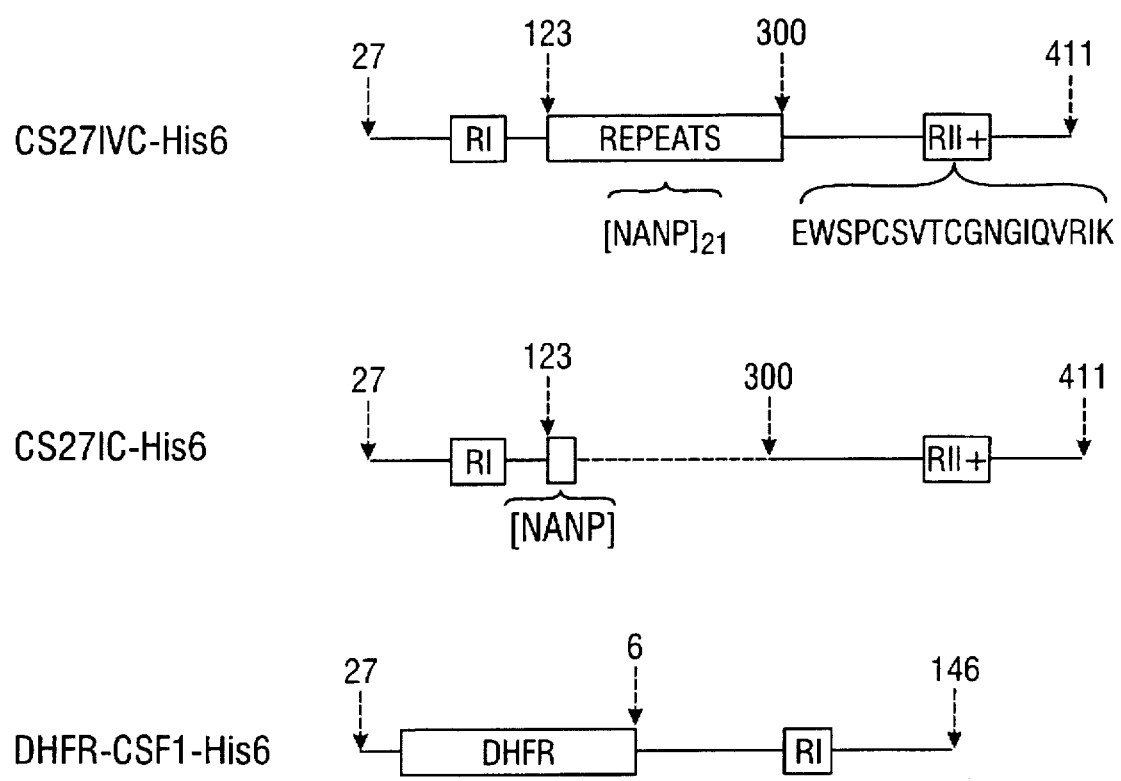

United States Patent [19]
Kuo et al.

[11] Patent Number: 5,766,899
[45] Date of Patent: Jun. 16, 1998

[54] TARGETED NUCLEIC ACID DELIVERY INTO LIVER CELLS

[75] Inventors: M. Tien Kuo; Zhi-Ming Ding, both of Houston, Tex.

[73] Assignee: Board of Regents, The University of Texas System, Austin, Tex.

[21] Appl. No.: 395,602

[22] Filed: Feb. 27, 1995

[51] Int. Cl.$^6$ .......................... C07K 7/08; C07K 14/00; C12N 15/11; C12N 15/85

[52] U.S. Cl. .................. 435/172.3; 435/235.1; 530/300; 530/324; 530/326; 530/350; 536/23.1; 536/24.5

[58] Field of Search .................. 530/300, 326, 530/324, 350; 514/2, 44; 536/23.1, 24.1, 24.5; 435/235.1, 172.3; 424/93.1

[56] References Cited

U.S. PATENT DOCUMENTS 5,399,346  3/1995  Anderson et al. ............... 424/93.21

FOREIGN PATENT DOCUMENTS 0259904  8/1987  European Pat. Off. .
0273085  12/1988  European Pat. Off. .

OTHER PUBLICATIONS

Ding ZM, et al. "Matarial circumsporozoite protein is a novel gene delivery vehicle to primary hepatocyte cultures and cultured cells." JBC 270 (8): 3667–3676, Feb. 24, 1995.

Stull RA, et al. "Antigene, ribozyme and aptamer nucleic acid durgs: Progress and prospects." Pharmaceutical Res. 42: 465–483, 1995.

Gura T. "Antisense has growing pains. " Science 270: 575–577, Oct. 27, 1995.

Orkin SH, et al. "Report and recommendations of the panel to assess the NIH investment in research on gene therapy. " Dec. 7, 1995.

Cerami, et al., "The Basolateral Domain of the Hepatocyte Plasma Membrane Bears Receptors for the Circumsporozoite Protein of Plasmodium falciparum Sporozoites, " *Cell*, 70:1021–1033 (Sep. 1992).

Cotten, et al., "High–efficiency receptor–mediated delivery of small and large (48 kilobase gene constructs using the endosome–disruption actifity of defective or chemically inactivated adenovirus particles." *Proc. Natl. Acad. Sci. USA*, 89:6094–6098 (Jul. 1992).

Cristiano, et al., "Hepatic gene therapy: Adenovirus enchancement of receptor–mediated gene delivery and expression in primary hepatocytes, " *Proc. Natl. Acad. Sci. USA*, 90:2122–2126 (Mar. 1993).

Cristiano, et al., "Hepatic gene therapy: Efficient gene delivery and expression in primary hepatocytes utilizing a conjugated adenovirus–DNA complex, " *Proc. Natl. Acad. Sci. USA*, 90:11548–11552, (Dec. 1993).

Dame, et al., "Structure of the Gene Encoding the Immunodominant Surface Antigen on the Sporozoite of the Human Malaria Parasite *Plasmodium falciparum*, "*Science*, 225:593–599 (Aug. 1984).

Ding, et al., "Malarial Circumsporozoite Protein Is a Novel Gene Delivery Vehicle to Primary Hepatocyte Cultures and Cultured Cells, " *Jrl. of Bio. Chem.*, 270, No. 8:3667–3676 (Feb. 1995).

Gottschalk et al., "Folate receptor mediated DNA delivery into tumor cells: potosomal disruption results in enhanced gene expression. " *Gene Ther.* 1:185–191 (1994).

Grossman, et al., "Retroviruses: delivery vehicle to the liver, " *Current Opinion in Genetics and Development*, 3:110–144 (1993).

Huber, et al., "Provocative Gene Therapy Strategy for the Treatment of Hepatocellular Carcinoma, " *Hepatology Elsewhere*, vol. 16, 1:273–274 (1992).

Huckett, et al., "Evidence for Targeted Gene Transfer by Receptor–Mediated Endocytosis; Stable Expression Following Insulin–Directed Entry of *NEO* into HepG2 Cells, " *Bio. Pharm.*, vol. 40, 2:253–263 (1990).

Kay, et al., "Gene therapy for metabolic disorders, " *TIG*, vol. 10, 7:253–257 (1994).

Kay, et al., Hepatic Gene Therapy: Persistent Expression of Human α1–Antitrypsin in Mice after Direct Gene Delivery In Vivo.*Human Gene Therpy*, 3:641–647 (1992).

Komoriya, et al., "Biologically active synthetic fragments of epidermanl growht factor: Localization of a major receptor–binding region," *Proc. Natl. Acad. Sci.*,USA vol. 81:1351–1355 (Mar.1984).

Kuriyama, et al., "A Potential Approach for Gene Therapy Targeting Hepatoma Using a liver–Specific Prmooter on a Retroviral Vector, " *Cell Struct. and Func.*, 16:503–510 (1991).

Makdisi, et al., "Methods of Gene Transfer Into Hepatocytes: Progress Toward Gene Therapy. " *Progress in Liver Diseases*, X:1 (1992).

Nielsen, et al., "Expression of a preproinsulin–β–galactosidase gene fusion in mammalian cells, " *Proc. Natl. Acad. Sic. USA*, 80:5198–5202 (1983).

Rich, et al., "Cell–Adhesive Motif in Region II of Malarial Circumsporozoite Protein, " *Science*, 249:1574–1577 (Sep. 1990).

(List continued on next page.)

*Primary Examiner*—Douglas W. Robinson
*Assistant Examiner*—Amy J. Nelson
*Attorney, Agent, or Firm*—Arnold, White & Durkee

[57] ABSTRACT

Disclosed is a receptor-mediated complex that selectively delivers nucleic acid into hepatocytes. Circumsporozoite (CS) protein is the targeting ligand that recognizes a receptor expressed on the liver cell surface. The CS ligand is complexed with a polylysine component that can bind nucleic acid. The level of gene expression is greatly enhanced when the complex is cotransfected with adenovirus. Using the present invention, a reporter gene was successfully transferred into a number of different cell lines that express high levels of receptor. The ability to introduce nucleic acid into specific mammalian cells is an important therapy for numerous diseases such as cancer, malaria and hepatitis.

29 Claims, 15 Drawing Sheets

OTHER PUBLICATIONS

Trubetskoy, et al., "Use of N-Terminal Modified Poly9L-lysine) -Antibody Conjugeate as a Carrier for Targeted Gene Delivery in Mouse Lung Endothelial Cells," *Bioconjugate Chem.*, 3:323–327 (1992).

Wagner, et al., "Influenza virus hemagglutinin HA-2 N-terminal fusogenic peptides augment gene transfer by transferrin–polylysine–DNA complexes: Toward a synthetic virus–like gene–transfer vehicle," *Proc. Natl. Acad. Sci. USA* 89:7934–7938 (Sep. 1992).

Wagner, et al., "Transferrin–polycation conjugates as carriers for DNA uptake into cells," *Proc. Natl. Sci. USA*, 87:3410–3414 (May 1990).

Wu, et al., "Receptor–mediated Gene Delivery in Vivo," *Jrnl. of Bio. Chem.*, vol. 266, 22:14338–14342 (1991).

Wu, et al., "Receptor–mediated in Vitro Gene Transformation by a Soluble DNA Carrier System," *Jrnl. of Bio. Chem.*, vol. 262, 10:4429–4432 (1987).

TARGETED NUCLEIC ACID DELIVERY INTO LIVER CELLS

The government owns rights in the present invention pursuant to grants CA 55813, DK49091 and CA11672 awarded by the National Institutes of Health.

BACKGROUND OF THE INVENTION

1. Field of the Invention

The present invention relates generally to the field of gene delivery. In particular, the invention relates to receptor-mediated gene targeting to hepatic cells. In one example, the invention relates to malarial circumsporozoite (CS) protein-mediated DNA delivery and expression in hepatocytes and other cell lines.

2. Description of the Related Art

The liver plays a vital role in the metabolism of proteins, lipids, carbohydrates, and vitamins. The kinds and the amounts of enzymes secreted by the liver directly control the metabolic pathways. The expression of many of these enzymes are controlled by a single gene. The defect of the gene may result in crippling of the metabolic processes and thus induce genetic and metabolic diseases. For example the defect of low density lipoprotein receptor gene results in familial hypercholesterolmia (FH); the defect of phenylalanine hydroxylase gene causes phenylketonuria (PKU); and the defect of gene for factor IX inductes hemophilia. So far there is no therapeutic method that can cure these diseases.

Furthermore, hepatocellular carcinoma (HCC) is one of the most common human solid malignancies and also one of the most lethal diseases with a mortality index of 0.92 (Rustigi, 1988). For the last two decades, the cure rate for this disease has not improved, indicating that the current treatment modalities are inadequate. While many cancer chemotherapeutic agents have a selectivity for cancer cells over normal cells, they have almost no defined tissue specificity. Surgical operations for HCC can seldom be performed due to the complication of liver cirrhosis. Therefore, innovative therapeutic approaches are needed that kill hepatoma cells selectively.

Recent advances in recombinant DNA and gene delivery technologies (Miller, 1992; Mulligan, 1993) suggest that gene therapy may be a promising alternative to standard radio- and chemotherapeutic regimens. This is particularly true for receptor-mediated gene delivery systems (Morgan and Anderson, 1993).

Receptor-mediated gene targeting takes advantage of the selective uptake of macromolecules by receptor-mediated endocytosis in almost all eukaryotic cells. Because of the cell type-specific distribution of various receptors, the delivery can be highly specific (Wu and Wu, 1993). Furthermore, in comparison with viral delivery systems (Morgan and Anderson, 1993), receptor-mediated gene delivery allows greater flexibility of DNA size and sequence because the DNA to be delivered does not need to be packaged into viral capsids. This helps avoid tedious clonal selection and virus-production processes. These characteristics make the system an attractive prospect for human gene therapy.

Receptor-mediated gene targeting vehicles consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein has been used as a gene delivery vehicle which recognizes the same receptor as ASOR (Ferkol et al., 1993; Perales et al., 1994). In vivo, the distributions of ASOR and transferrin receptors are very different. Transferrin receptors are found in many different cell types, while ASOR receptors are almost exclusively distributed on the sinusoidal domain of the hepatocytes (Wu and Wu, 1987).

Much attention has been focused on the development of ASOR as a hepatic gene delivery vehicle due to its unique distribution. ASOR-mediated hepatic gene delivery system has not been perfected, however, mainly because of poor efficiency. The efficiency is influenced by the physiology of endogenous ASOR and its receptors (Schwarts and Rup, 1983, Spiess and Lodich, 1985). In certain diseases there is an accumulation of ASOR due to down regulation of ASOR receptor. This is particularity true for individuals with hepatitis (Arima et al., 1977), liver cirrhosis (Marshall et al., 1974), hepatocellular carcinomas (Marshall et al., 1974; Marshall et al., 1978), and diabetes mellitus (Dodeur et al., 1982).

The malaria circumsporozoite (CS) protein has been shown to play an important role in the invasion of liver by malaria parasite (Nussenzweig and Nussenzweig, 1989; Miller et al., 1994). It is known that this hepatic invasion is not infectious and that malaria symptoms manifest during the erythrocyte cycle (Miller et al., 1994). Much attention has been paid to CS for its use as a target for intervention of malaria infection, particularly in the vaccine development (Nussenzwig and Long, 1994).

A gene delivery system utilizing a receptor-mediated DNA delivery vehicle specific for liver cells would prove to be an important therapy for liver cancer, as well as for numerous genetic and metabolic disorders and infectious diseases such as hepatitis, and malaria. The specificity of cell recognition and rapid invasion of the malaria CS protein raises the possibility of using this liver specific ligand for hepatic gene delivery vehicle. The discovery of an improved therapy specific for liver disease would have considerable global impact.

SUMMARY OF THE INVENTION

The present invention addresses the need for improved therapy for liver cancer and other liver-associated diseases by providing a receptor-mediated delivery vehicle to target and deliver nucleic acid into liver cells. In particular, the present invention concerns a nucleic acid-binding agent/ligand complex that selectively delivers nucleic acid into liver cells employing the circumsporozoite (CS) protein of malaria. The present invention also provides compositions and methods to promote the uptake and expression of the nucleic acid/ligand complex into cells by the use of an endosomal lysis agent.

The present invention concerns a complex comprising of a circumsporozoite region II-containing polypeptide and a nucleic acid-binding agent. In preferred embodiments, the ligand is selected from the group consisting of: CS27IVC-His$_6$, CS27IC-His$_6$, EWSPCSVTCGNGIQVRIK (SEQ ID NO:1) and EWSPCSVTCGNGIQVRIKPGSAN (SEQ ID NO:2).

In one embodiment of the invention, the nucleic acid-binding agent is a polycationic moiety. In a further embodiment of the invention the nucleic acid-binding agent is polylysine. In preferred embodiments, the invention includes an endosomal lysis agent. In a particular embodiment the endosomal lysis agent is an infectious, replication-deficient adenovirus.

Complexes according to the present invention further comprise a nucleic acid. In particular embodiments, the nucleic acid may encode a therapeutic gene. In a preferred embodiment, the therapeutic gene may be a cDNA. In another embodiment, the therapeutic gene may comprise a promoter that is active in a cell, expressing a CS protein receptor, and operably linked to said therapeutic gene. In a further embodiment, the therapeutic gene is a tumor suppressor. In further embodiments, the therapeutic gene is cystic fibrosis transmembrane conductance regulator (CFTR) or a low density lipoprotein receptor or a phenylalanine hydroxylase or blood clotting factor IX.

The invention may further comprise a nucleic acid encoding an antisense construct. In an exemplary embodiment of the invention, the antisense construct may correspond to an oncogene transcript. In another exemplary embodiment of the invention, the antisense construct may correspond to an hepatitis virus transcript. In yet another exemplary embodiment of the invention, the antisense construct may correspond to a malaria transcript.

The invention may also comprise a nucleic acid encoding an ribozyme. In an exemplary embodiment of the invention, the ribozyme may correspond to an oncogene transcript. In another embodiment of the invention, the ribozyme may correspond to an hepatitis virus transcript. In yet another embodiment of the invention, the ribozyme may correspond to a malaria transcript.

In a further embodiment, the invention includes a pharmaceutical composition comprising a complex and a pharmaceutically-acceptable carrier, diluent or excipient. Another embodiment of the invention includes a kit comprising of a ligand, comprising a circumsporozoite region II-containing polypeptide and a nucleic acid-binding agent. In a preferred embodiment of the invention the ligand and nucleic acid-binding agent are complexed. The kit may further comprise of a nucleic acid encoding a therapeutic gene. In a preferred embodiment of the invention the ligand, nucleic acid-binding agent and nucleic acid are complexed.

Another embodiment of the invention includes a method of delivering a gene to a cell. This method comprises providing a complex for the delivery of a gene to a cell and contacting said complex with said cell.

In a further embodiment of the invention, a method of delivering a gene to a cell comprises contacting said cell with an endosomal lysis agent. In a preferred embodiment of the invention, the endosomal lysis agent may be an infectious, replication-deficient adenovirus.

In a further embodiment of the method of delivering a gene to a cell, said gene is a cDNA. In a preferred embodiment of the invention, the cDNA further comprises a promoter that is active in said cell and operably linked to said gene.

Another embodiment of the invention includes a method of treating a mammal with an hepatic cell-associated pathologic condition in vivo comprising providing a pharmaceutical composition and administering said pharmaceutical composition to said mammal.

Preferred embodiments of the invention, include the said method of treating a mammal with an hepatic cell-associated pathologic condition in vivo, wherein said pathologic condition is selected from the group consisting of cancer, hepatitis, malaria, cystic fibrosis, familial hypercholesterolemia, phenylketonuria and hemophila.

Further embodiments of the invention include a method of treating a mammal with an hepatic cell-associated pathologic condition in vivo, wherein said therapeutic gene is an antisense construct or a ribozyme.

Yet further embodiments of the invention include a method of treating a mammal with an hepatic cell-associated pathologic condition in vivo, wherein said pharmaceutical composition further comprises an endosomal lysis agent. A preferred embodiment of the invention includes an endosomal lysis agent comprising of an infectious, replication deficient adenovirus.

A final embodiment of the invention includes a method of treating a mammal with a pathologic condition comprising of a composition, in a pharmaceutically acceptable form, and contacting a mammalian cell with said composition and administering said cell to said mammal.

The said mammalian cell may be obtained from an animal, contacted to said composition and then either; readministered to the said animal or; administered to a distinct animal.

BRIEF DESCRIPTION OF THE DRAWINGS

FIG. 1. Schematic representation of the recombinant CS proteins. The major functional regions of CS protein, region I (RI), region II+ (RII+), and repeat region (REPEATS) which contains 21 [NANP] amino acid residues are indicated. The numbers shown above the constructs represent amino acid sequences from *P. falciparum* CS protein. DHFR-CSF1-His6 is the fusion protein of mouse dihydrofolate reductase (DHFR) and CS peptides. The 18 amino acid residues shown below RII+ is a CS epitope recognized by the receptor EWSPCSVTCGNGIQVRIK (SEQ ID NO:1).

FIG. 2A. Purification of CS/polylysine and transferrin/polylysine conjugates. CS27IVC-His6/polylysine and transferrin/polylysine were conjugated by EDC. The reaction mixtures were then passed through a Superose 6 column. Details are described in Example 1. Chromatographic eluting profiles of $^3$H-CS27IVC-His6 and CS27IVC-His6/polylysine conjugate.

FIG. 2B. Purification of CS/polylysine and transferrin/polylysine conjugates. Eluting profiles of fluorescein isothiocyanate (FITC)-polylysine and FITC-polylysine conjugated by EDC. The fluorescence intensity was determined by a fluorometer at excitation 490 nm and emission 530 nm.

FIG. 2C. Purification of CS/polylysine and transferrin/polylysine conjugates. The elution profiles of transferrin and transferrin/polylysine conjugate.

FIG. 2D. Purification of CS/polylysine and transferrin/polylysine conjugates. Acid-urea gel electrophoretic analyses of proteins eluted from the CS/polylysine. Unconjugated CS, polylysine (PLL) and mixture of CS and PLL (CS/PLL) were run as references.

FIG. 2E. Purification of CS/polylysine and transferrin/polylysine conjugates. Transfection efficiencies of protein fractions corresponding to the eluting profile shown in FIG. 2D. Six μg of pCMV-β-gal plasmid DNA were complexed with 5.8 μg of CS-PLL conjugate from each fraction. DNA complexes were used to transfected HepG2 cells in the presence of adenovirus ($5\times10^3$ particles/cell). The results were calculated from duplicated samples, 800–1,000 cells in three random fields were counted.

FIG. 2F. Purification of CS/polylysine and transferrin/polylysine conjugates. Acid-urea gel electrophoretic analyses of proteins eluted from the transferrin/polylysine. Unconjugated protein transferrin (Tf), polylysine (PLL) and mixture of Tf and PLL (Tf/PLL) were run as references.

FIG. 2G. Purification of CS/polylysine and transferrin/polylysine conjugates. Transfection efficiencies of protein fractions corresponding to the eluting profile shown in FIG. 2F. Six μg of pCMV-β-gal plasmid DNA were complexed with 4.2 µg of transferrin-PLL from each fraction. DNA complexes were used to transfected HepG2 cells in the presence of adenovirus (5×10³ particles/cell). The results were calculated from duplicated samples. 800–1,000 cells in three random fields were counted.

Figure 3:
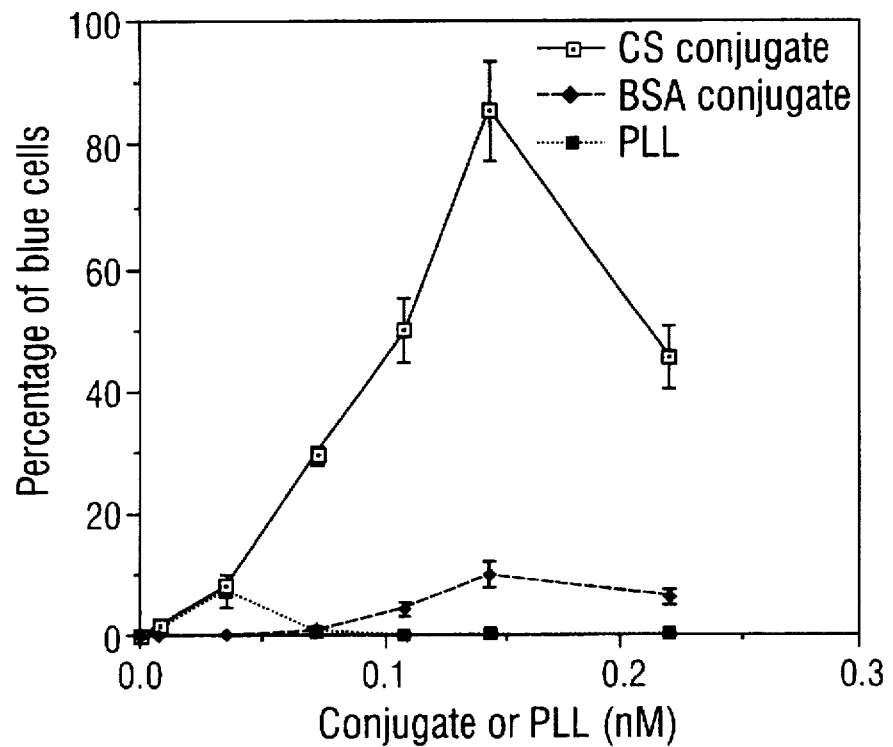

FIG. 3. Effects of CS-polylysine conjugate concentrations on the expression of β-galactosidase in primary hepatocytes. Different amounts of CS conjugate. BSA conjugate and polylysine were complexed with 6 µg of pCMV-b-gal DNA as described in Materials and Methods. Example 2. Primary hepatocytes (3×10⁵) were transfected with the complexes in the presence of adenovirus (4×10⁴ particles/cell). The cells were stained with X-gal and percent of blue cells were determined by visually counting 800 to 1000 cells from three random fields for each duplicated samples.

Figure 4:
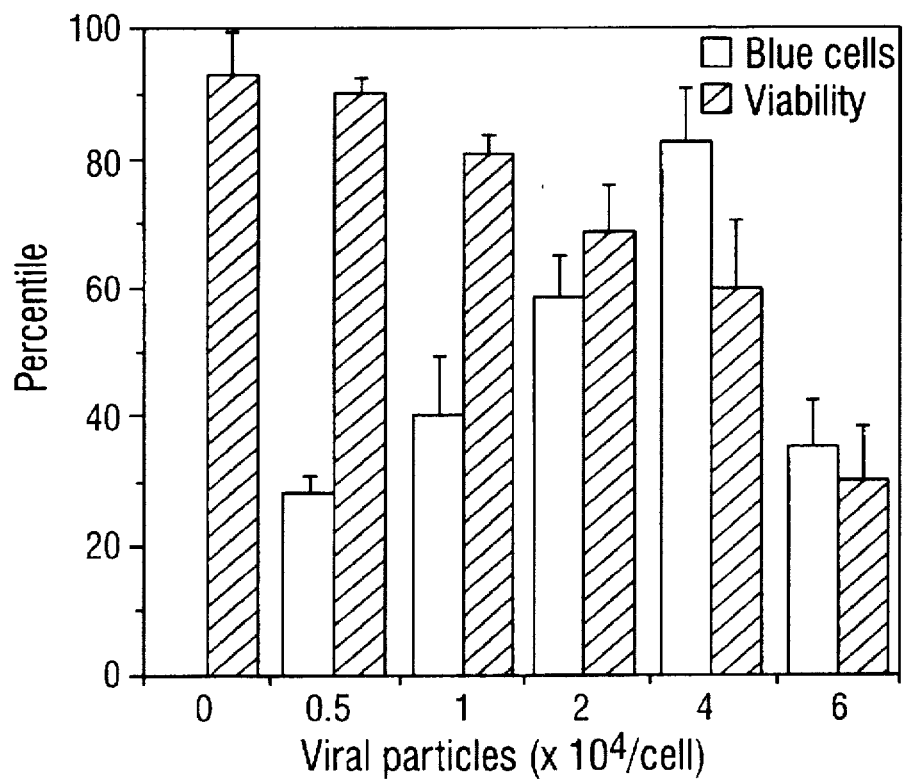

FIG. 4. Effects of adenovirus concentration on the expression of β-galactosidase in primary hepatocytes. CS27IVC-His6 conjugate (7.4 µg) was complexed with 6 µg pCMV-β-gal DNA. Indicated amount of adenovirus was added to the cells after the addition of the complex. Eighteen hours after transfection. cell viability and β-galactosidase activity were determined by trypan blue exclusion and X-gal stains respectively. Data were collected by counting 800 to 1000 cells from three random fields for each triplicated samples.

Figure 5:
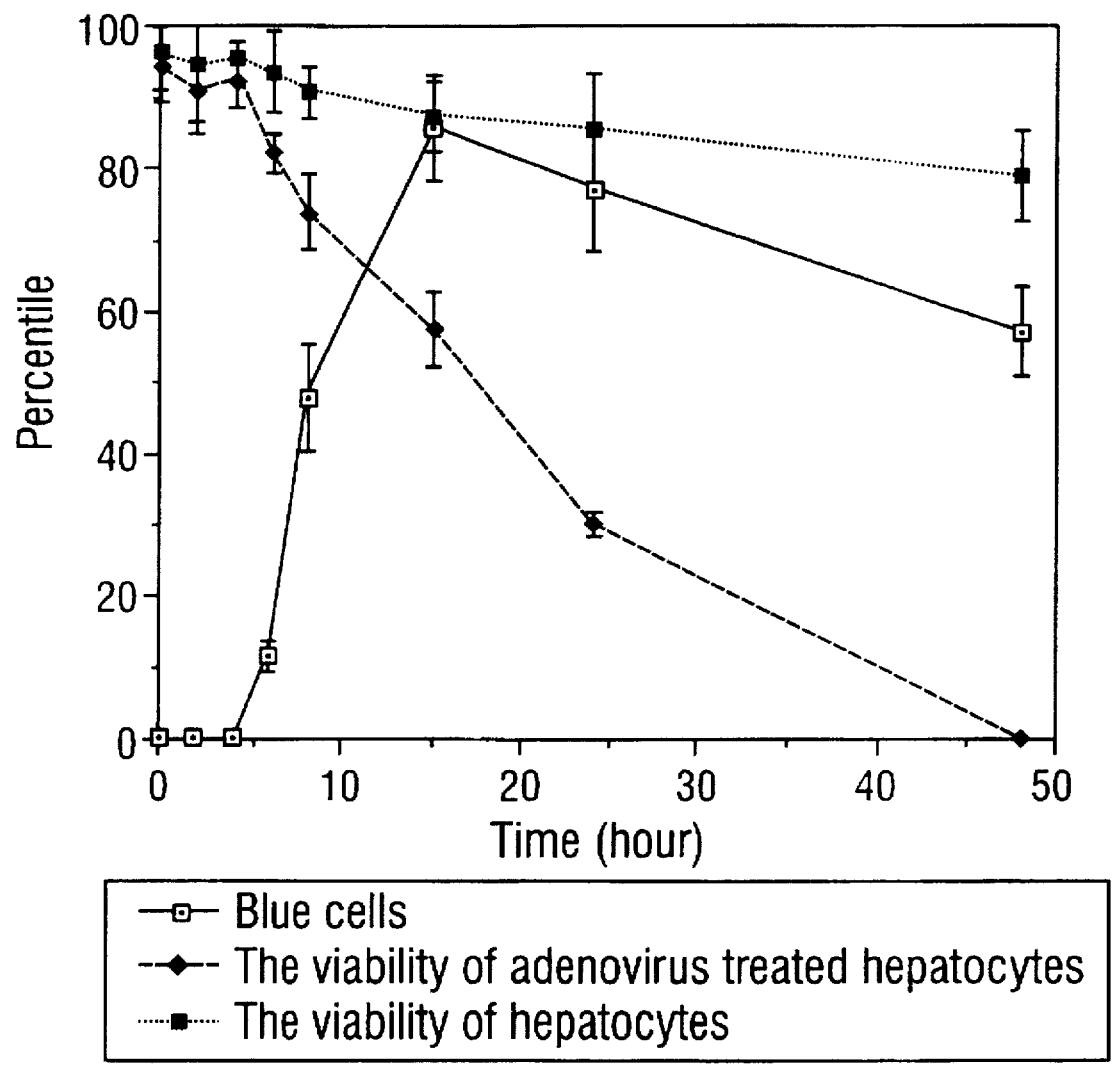

FIG. 5. Kinetics of β-galactosidase expression and cell viability after transfection with DNA complex. CS27IVC-His6 conjugate (7.4 µg) was complexed with 6 µg of pCMV-β-gal DNA. The transfection of primary hepatocytes was initiated (time 0) by the addition of the DNA complexes and adenovirus (4×10⁴ particles/cell). At different time intervals, percent of blue cells (β-galactosidase expression) and cell viability were determined as described in the legend to FIG. 4. The plating efficiencies of hepatocytes were also included. The data were not normalized against the plating efficiencies.

Figure 6A:
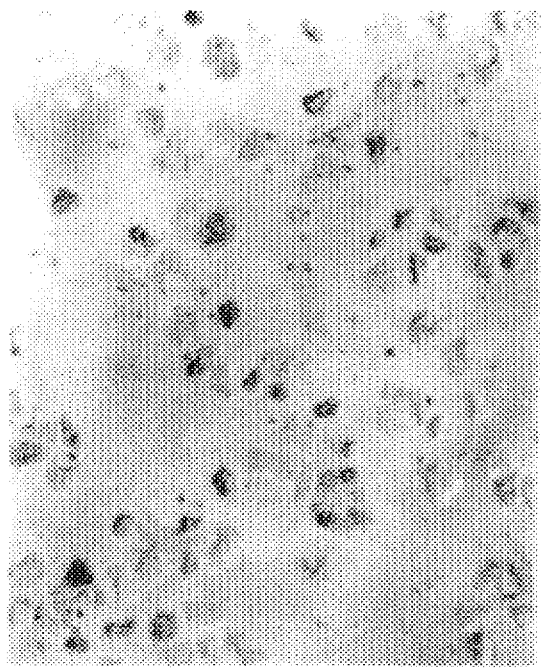
Figure 6B:
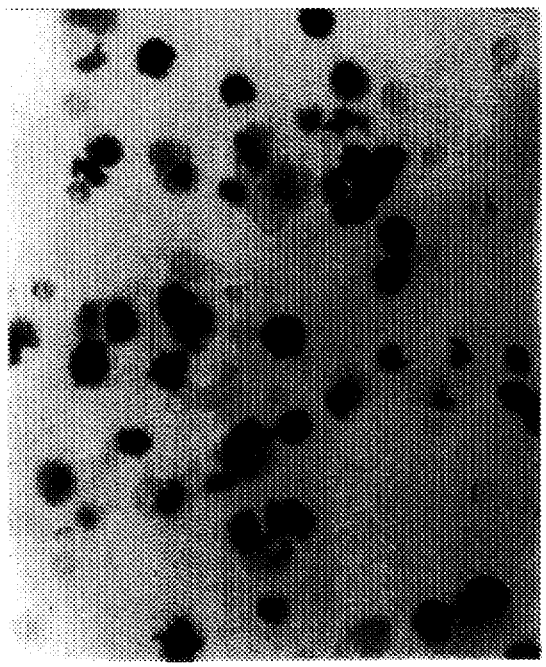

FIG. 6. Expression of β-galactosidase in primary hepatocytes after transfected with DNA complexes containing different recombinant CS proteins. CS conjugates containing CS27IVC-His6 (b). CS27IC-His6 (c) and DHFR-CSF1-His6 (d) were complexed with 6 µg pCMV-β-gal DNA. The amount of CS conjugate used were determined in prestudies. Transfection was carried out in the presence of adenovirus (4×10⁴ particles/cell). β-galactosidase was determined by X-gal staining. Six µg pCMV-β-gal DNA was used as control (a).

Figure 7:
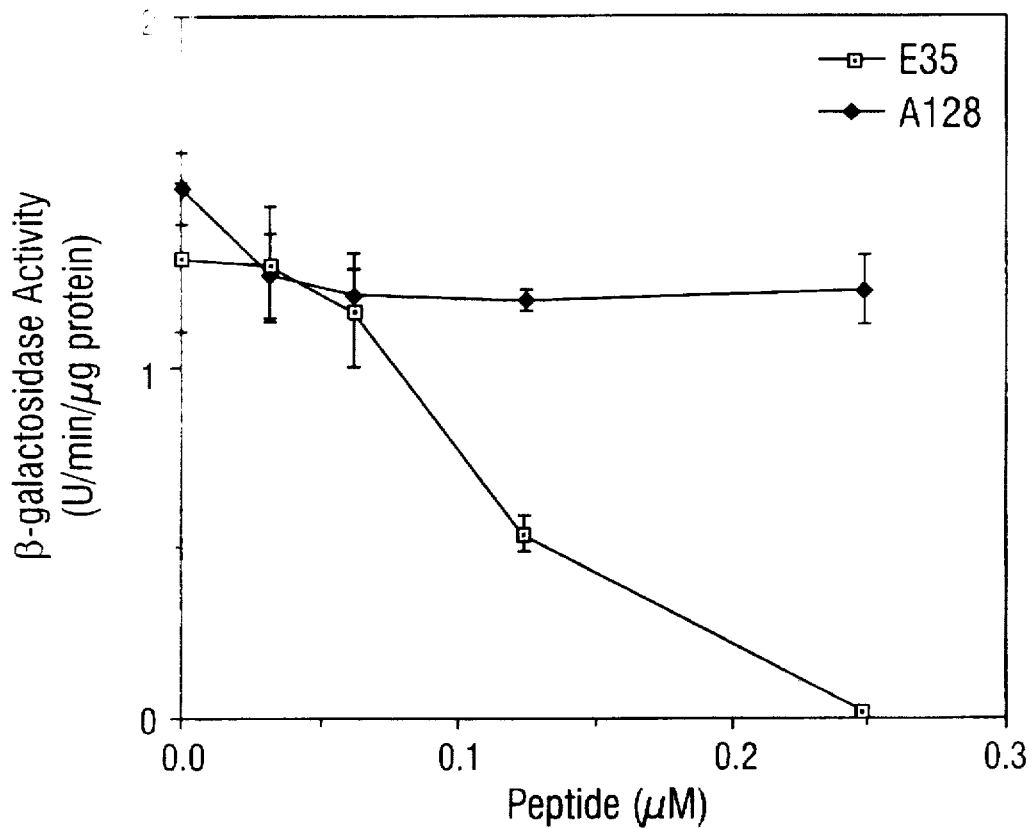

FIG. 7. Influence of region II CS peptide on the expression of β-galactosidase in primary hepatocytes. CS27IVC-His6 conjugate (7.4 µg) was conjugated to 6 µg of pCVMV β-gal DNA. Different amounts of E35 and A128 peptides were added to cells after the addition of DNA complexes and adenovirus (4×10⁴ particles/cell). β-galactosidase activity was quantitated using ONPG as a substrate. Results were from triplicate studies.

FIG. 8. Expression of β-galactosidase in different cell lines transfected with CS carrier. CS27IVC-His6 conjugate (7.4 μg) was complexed with 6 μg of pCVMV β-gal DNA. The DNA complex was used to transfect HeLa, NIH 3T3, CHO, Hepa G2, and HL-60. The viral concentration for each cell line was optimized. β-galactosidase activity was quantified as described in Example 2 using ONPG as a substrate. Data were average of triplicated studies.

FIG. 9 Uptake of CS27IVC-His6 by primary hepatocytes and HL-60 Cells. $^3$H-CS27IV-His6 (2.5 μg) was mixed with 0.5 ml serum free medium and added to the cells. At different time intervals, the medium was removed. The cells were washed three times with PBS and lysed with 0.5 ml of 0.5N NaOH. The radioactivity was measured by liquid scintillation counter.

FIG. 10A. Uptake of DNA complex by primary hepatocytes CS27IVC-His6 (3.7 μg), transferrin (2.9 μg), and BSA (2.75 μg) conjugates were complexed with 3 μg of $^{32}$P-labeled DNA prepared by mixing 10 ng nick-translated DNA with 2.99 μg cold DNA. The complexes were added to $5\times10^5$ cells. Data were from triplicate samples.

FIG. 10B. Uptake of DNA complex by HL-60 cells. CS27IVC-His6 (3.7 μg), transferrin (2.9 μg), and BSA (2.75 μg) conjugates were complexed with 3 μg of $^{32}$P-labeled DNA prepared by mixing 10 ng nick-translated DNA with 2.99 μg cold DNA. The complexes were added to $5\times10^5$ cells. Data were from triplicate samples.

DETAILED DESCRIPTION OF THE PREFERRED EMBODIMENTS

Receptor-Mediated Delivery Vehicle

In one embodiment the present invention includes a complex comprising a ligand and a nucleic acid-binding agent. As used herein, a complex can be defined as one or more molecules bound together by any physical or chemical means. The complex may be tightly or weakly bound together in a highly specific or totally non-specific way.

As used herein, the term "ligand" is intended to refer to any molecule that binds to another molecule or macromolecule. The phrase "nucleic acid-binding agent" is intended to refer to any molecule or compound that binds nucleic acid. A ligand and nucleic acid-binding agent may be "complexed" together by any means including; covalent, ionic, hydrophobic, intercalative, van der Waals' or a combination of these forces and others. One embodiment of the invention includes coupling a ligand and nucleic acid-binding agent together. A preferred embodiment may use agents such as carbodiimides, N-succinimidyl,3-(2-pyridyldithio) propionate, succinimmidyl, 4-(N-maleimidomethyl) cyclohexane-1-carboxylate, diisocyanates, glutaraldehyde, diazobenzenes, and hexamethylene diamines. This list is not intended to be exhaustive of the various coupling agents known in the art but, rather, is exemplary of the more common coupling agents that may be used.

In the present invention the ligand comprises a malarial protein known as circumsporozoite (CS) and in particular, the region II of CS. CS covers the surface membranes of malarial sporozoites and includes region II, a conserved region of amino acids identical in all species of malaria sporozoites (Rich et al., 1990). It is this region of the circumsporozoite that specifically recognizes and binds to the receptor on the cell surface.

The cognate receptor protein for CS is expressed on the surface of hepatocytes. A number of non-hepatocytic cell lines also express a receptor recognizable by the circumsporozoite region II-containing polypeptide (Examples 4 and 5, Rich et al., 1990). However, in vivo studies have demonstrated that CS receptors are not found in the tissues from which these cultured cells are established (Rich et al., 1990). These results suggest that CS protein receptor biosynthesis can be upregulated during in vitro culture conditions. While the present invention is exemplified through the use of the specific binding of the circumsporozoite region II-containing polypeptide to its hepatic receptor, it is proposed that the invention is generally applicable to any situation where a CS region II-containing polypeptide recognizes a receptor. In this regard, cell types such as myeloid, T and B cells are mentioned by way of example.

In order to function in connection with the present invention, all that is required is that such a circumsporozoite region II-containing polypeptide binds to a CS receptor, preferably a CS receptor expressed on a cell surface, and in particular a CS receptor expressed on a liver cell surface. This may be tested by any of the many binding assays in the art, for example; gel retardation assays, filter binding techniques, affinity chromatography and precipitation or sedimentation methods.

In order to determine if the peptide binds to a CS receptor one would label the protein, polypeptide or peptide to be tested and admix with CS receptor or a cell expressing the receptor on its cell surface, under conditions which allows binding. This mixture would then be submitted to conditions that separate the unbound peptide from bound peptide such as electrophoretic gels, column chromatography, membrane filtration or centrifugal force through a suitable medium. The amount of protein, polypeptide or peptide that bound to the CS could be determined and compared with a control sample comprising of a peptide with no specific binding affinity for the CS receptor or a cell line lacking the CS receptor. Further binding studies may be performed, including CS region II-containing polypeptides as competitors, to compare affinities for receptor.

Accordingly, functional assays to detect binding and cellular uptake of a complex via the CS receptor can be performed using reporter genes and in vitro cellular systems, as described in the disclosed examples.

Preferred embodiments of the invention include proteins or polypeptides comprising of structures such as CS27IVC-His$_6$ or CS27IC-His$_6$ as described herein. Even more preferred embodiments include any protein, polypeptide or peptide that contains region II as exemplified by EWSPCS-VTCGNGIQVRIK (SEQ ID NO:1) and EWSPCS-VTCGNGIQVRIKPGSAN (SEQ ID NO:2), or any modified or changed protein, polypeptide or peptide that is substantially equivalent to these sequences as described below in the section on Biological Functional Equivalents.

Furthermore, CS region II bears a striking homology to a cell adhesion domain of thrombospondin (Prater et al., 1991; Tuszynski et al., 1989) and to regions of several other proteins (Clarke et al., 1990; Hedstrom et al., 1990; Robson et al., 1988; Goundis and Reid, 1988). It will be understood that to the extent that these proteins are recognized by the CS protein receptor then such proteins may be used in the same manner as the peptides of the invention and hence are also functional equivalents.

The invention also concerns a nucleic acid-binding agent. Nucleic acid-binding agents may be proteins, polypeptides, peptides, antibodies, nucleotides, carbohydrates, fatty acids, organic or inorganic compounds or a combination of these and others. Nucleic acid-binding agents may bind to single stranded or double stranded DNA, or to single stranded or double stranded RNA, by chemical or physical forces or by a combination of the two. A nucleic acid-binding agent may bind to the nucleic acid itself, bind to the nucleic acid and bind to another molecule forming a bridge between the two or, bind nucleic acid to another molecule in a reaction that does not require the agent to be part of the complex.

In order to function according to the present invention all that is required is that an agent binding to nucleic acid directly or indirectly must be complexed to a CS ligand in such a manner that allows recognition of the CS ligand by a cell expressing a CS receptor. In a preferred embodiment, this recognition includes internalization of the CS ligand complex via normal receptor-mediated endocytosis. In an even preferred embodiment this recognition and internalization delivers the nucleic acid into a cell for expression of, or recombination with, the target endogenous nucleic acid.

In one embodiment, the nucleic acid-binding agent may insert itself between base pairs in an intercalative manner or bind in the minor or major groves. This binding may be totally non-specific or specific for base pair sequences. In further embodiments, nucleic acids may be cross linked with other molecules with chemically of photochemically reactive groups.

In another embodiment of the invention, the nucleic acid-binding agent covalently links the nucleic acid to another molecule. In a preferred embodiment the nucleic acid-binding agent is one of the coupling agent as described above. In an even more preferred embodiment the nucleic acid-binding agent is carbodiimide. However, covalent coupling of the nucleic acid may alter its specificity and preclude proper gene expression or target nucleic acid recognition. The same is true of many intercalators or cross-linkers. Therefore, a preferred embodiment of the invention is a polycationic moiety that depends on electrostatic-dominated binding involving sequence-neutral interactions between the cationic groups and the negatively charged phosphates on nucleic acid. The polycationic moiety binds DNA strongly resulting in the formation of a toroid complex where the negative charge of nucleic acid molecule is completely neutralized. This soluble toroid complex may be internalized via normal receptor-mediated endocytosis. In certain embodiments, these polycationic moieties, may include the natural polyamine such as spermine and spermidine. In a preferred embodiment, the polycationic moiety may be an artificially produced moiety, such as polylysine.

In order for the invention to function properly, certain criteria with regard to the nucleic acid-binding agent need to be fulfilled. First, the nucleic acid to be delivered into the cell must bind to the nucleic acid-binding agent without loosing its integrity in any way. Second, the complex comprising of ligand, nucleic acid-binding agent and nucleic acid must be in soluble form to allow greater accessibility of the complex to cells in vitro and in vivo. Third, once the complex is internalized within the host cell, the nucleic acid must have access to its target sequence while avoiding degradation.

In order to test a nucleic acid-binding agent, functional assays may be employed. Examples 1 through 5, as disclosed herein, explain how to detect whether nucleic acid is being delivered successfully into a cell via the CS receptor by the use of a reporter gene.

The present invention also concerns an endosomal lysis agent that serves to release the complex from endosomes once internalized by the cell before it fuses with lysosome to prevent degradation of the nucleic acid and/or the complex. An endosomal lysis agent is defined as any agent that causes a disruption of the endosome sufficient to allow release of a complex but without undue disruption of other cellular components. In one embodiment, adenoviral particles would be an affective endosomal lysis agent. The same efficacy of gene delivery may be achieved by coupling of adenovirus to the DNA complex.

In further embodiments, modified adenoviruses may be used to overcome any potential safety problems. For example an infectious, replication-deficient adenovirus, crippled adenovirus particle (Cotten et al., 1992) or less toxic adenovirus (Cotten et al., 1993) may be used.

Alternatively, in still further embodiments, fusogenic viral peptides can be used in lieu of adenovirus, since influenza hemagglutinin HA-2 terminal peptides have been demonstrated to augment gene transfer efficiency greater than 100-fold by the receptor-mediated gene transfer into HeLa cells (Wagner et al., 1992; Plank et al., 1994). In addition, recent studies in protein trafficking and endosomal physiology have identified several endogenous proteins associated with vesicle budding, membrane fusion (Rothman and Orci, 1992) and protein translocation (Girlich and Rapoport, 1993). These proteins could be used to enhance the expression of transgenes in a receptor-mediated gene delivery system.

Biological Functional Equivalents

As mentioned above, changes may be made in the structure of circumsporozoite region II-containing polypeptide while maintaining the desirable receptor-binding characteristics. For example, certain amino acids may be substituted for other amino acids in a protein structure without appreciable loss of interactive binding capacity with structures such as, for example, antigen-binding regions of antibodies or binding sites of ligands such as the circumsporozoite region II-containing polypeptide. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of a circumsporozoite region II-containing polypeptide (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. It also is well understood that where certain residues are shown to be particularly important to the biological or structural properties of a protein or peptide, e.g., residues in active sites, such residues may not generally be exchanged. This is the case in the present invention, where two cysteines (C) in region II are important for maintaining the high binding affinity of CS protein to its receptor. The deletion or mutation of either one of the cysteine or both will greatly reduce the binding activity. It is proposed that in solution, the two cysteine residues of region II form intra-chain disulfide bonds as well as disulfide-linked oligmers to maintain active conformation (Ceremi et al., 1992).

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

Structural Functional Equivalents and Sterically Similar Constructs

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

Targeted Therapeutic Gene Delivery

One aspect of the invention concerns the binding of a therapeutic gene to the circumsporozoite region II-containing polypeptide/nucleic acid binding agent. The term "therapeutic gene" is intended to refer to any foreign nucleic acid introduced into a cell for the potential benefit of the cell or the individual organism as a whole. This may include the introduction of: a normal allele of a gene into a cell that either does not express its own copy of the gene or has a defective copy; a normal or improved gene into a normal cell for the enhanced expression of a gene product; suppressor genes to correct any endogenous mutations within the cell; or the introduction of toxic genes into a cell to interfere with the expression of oncogenes or viral genes and thus inhibit neoplastic cell growth or viral replication. This also includes antisense constructs and ribozymes, described in more detail below.

In preferred embodiments, the therapeutic gene is stably integrated into the genome of the cell. This integration may be in the cognate location and orientation via homologous recombination (gene replacement) or it may be integrated in a random, non-specific location (gene augmentation). In further embodiments, the gene may be intransiently integrated in the cell as an independent segment of DNA.

In preferred embodiments, the therapeutic gene would comprise complementary DNA (cDNA). The term cDNA used here, is intended to refer to DNA prepared using messenger RNA (mRNA) as template. The advantage of using cDNA, as opposed to genomic DNA or DNA polymerized from a genomic DNA or non- or partially processed RNA template, is that the cDNA does not contain any non-coding sequences but encodes all the necessary information for translation of the corresponding protein. However, there may be times when the full or partial genomic sequence is preferred.

In still further embodiments, the cDNA would be operably linked to a promoter active in a cell, preferably in a cell that expresses a CS protein receptor and more preferably, in an hepatic cell. A "promoter", as used herein, is meant to refer to a sequence of DNA recognized by the synthetic components of the cell, required to initiate the specific transcription of a gene. What is meant by the phrase "operably linked" is that not only is the promoter recognized by the cell machinery for transcription of the specific therapeutic gene, but also it is in the correct location and orientation in relation to the gene to allow the promoter to function appropriately.

The particular promoter that is employed to control the expression of the therapeutic gene is not believed to be important, so long as it is capable of expressing the therapeutic gene in the targeted cell. Thus, where a human cell is targeted, it is preferable to position the therapeutic gene coding region adjacent to and under the control of a promoter that is capable of being expressed in a human cell. Generally speaking, such a promoter might include either a human or viral promoter. While the CMV is preferred, the invention is by no means limited to this promoter, and one may also mention by way of example promoters derived from RSV, N2A, LN, LNSX, LNSN, SV40 or LNCX (Miller, et al., 1989; Hamtzoponlos, et al., 1989). Preferred embodiments of the invention would include liver-specific promoters such as human albumin promoter and human phenylalanine hydroxylase promoter (Wang et al., 1994)

It is proposed that the invention is generally applicable to any situation where one desires high level expression of a recombinant protein in a target or host cell through the use of the invention. While the nature of the gene introduced is not critical to broader aspects of the invention, it should be mentioned that in the context of liver cancer treatment modalities, a particular example would be a tumor suppressor. There are numerous tumor suppressors well know to those in the art, preferred examples including p53, RB, APC, DCC, NF-1,NF-2, WT-1, MEN-I, MEN-II, BRCA1, VHL, FCC and MCC. This list is not intended to be exhaustive of the various tumor suppressors known in the art but, rather, is exemplary of the more common tumor suppressors.

On the other hand, the therapeutic gene may be directed to a non-cancerous disease state. For example cystic fibrosis (CF) is caused by mutations in the gene encoding the cystic fibrosis transmembrane conductance regulator (CFTR). Delivery of the CFTR gene into hepatocytes may prove to be an important therapy for CF. Furthermore, genetic therapy for hypercholesterolemia, phenylketonuria and hemophila could be achieved by introduction of a therapuetic gene. Table 1 lists examples of metabolic diseases. The underlying deficiency of these diseases may also be alleviated by the introduction of relevant genes using the present invention. The list is, of course, exemplary, and any therapeutic gene may be directed to any genetic or infectious disease, as well as metabolic disorder not mentioned here, and equally produce therapeutic results using the present invention.

TABLE 1

Examples of Metabolic Disease (Kay and Woo, 1994)

| Type of disorder | Example | Underlying deficiency |
| --- | --- | --- |
| Glycogen storage | Glycogen storage deficiency type 1A | Glucose-6-phosphatase |
| Gluconeogenesis | Pepck deficiency | Phosphoenolpyruvate-carboxykinase |
| Galactose metabolism | Galactosemia | Galactose-1-phosphate uridyl transferase |
| Aminoacidopathies | Phenylketonuria | Phenylalanine hydroxylase |
|  | Maple syrup urine disease | Branched chain α-keotacid dehydrogenase |
|  | Tyrosinemia type 1 | Fumarylacetoacetate hydrolase |
| Organic acidemias | Methylmalonic acidemia | Methyl malonyl-CoA mutase |
| Fatty acid metabolism | MCAD | Medium chain acyl CoA dehydrogenase |
| Urea cycle | OTC | Ornithine transcarbamylase deficiency |
|  | Citrullinemia | Argininosuccinic acid synthetase |
| Lipoprotein metabolism | Familial hypercholesterolemia | LDL receptor |
| Bilirubin metabolism | Crigler-Najjar | UDP-glucouronosyltransferase |
| Purine and pyrumidine metabolism | Severe combined immunodeficiency | Adenosine deaminase |
|  | Gout, Lesch-Nyan syndrome | Hypoxanthine guanine phosphoribosyl transferase |
| Vitamin metabolism | Biotinidase deficiency | Biotinidase |
| Lysosomal storage | Gaucher disease | β-Glucocerebrosidase |
|  | Sly syndrome | β-Glucuronidase |
| Peroxisomal disorders | Zellweger syndrome | Peroxisome membrane protein 70 kDa |

TABLE 1-continued

Examples of Metabolic Disease (Kay and Woo, 1994)

| Type of disorder | Example | Underlying deficiency |
| --- | --- | --- |
| Heme biosynthesis | Acute intermittent porphyria | Porphobilinogen deaminase |
| Genetic disease | Familial hypercholesterolemia | Low density lipoprotein deficiency |
| Genetic disease | Hemophila B | Factor 1x-deficiency |
| Cancer | Hepatocellular carcinoma | Virus (?), Oncogenes (?) |

Targeted Antisense Construct Delivery

In embodiments where inhibition or suppression of gene expression is desired, antisense molecules will be employed. In that the invention concerns a nucleic acid delivery vehicle, the invention is generally applicable to any antisense construct.

The term "antisense nucleic acid" is intended to refer to the targeting of oligonucleotides against complementary base sequences in DNA and RNA. Extracellular oligonucleotides enter the cell and specifically bind to their respective targets, interfering with transcription, RNA processing and transport, or translation. Targeting double-stranded (ds) DNA with oligonucleotide leads to triple-helix formation; targeting RNA will lead to double-helix formation.

For certain applications, the antisense DNA or RNA that is introduced will be complementary to a selected cellular gene, such as an oncogene sequence or some other sequence whose expression one seeks to diminish through antisense application.

While all or part of the coding sequence may be employed in the context of antisense construction, statistically, any sequence of 17 bases long should occur only once in the human genome and therefore suffice to specify a target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. Therefore sequences greater than 17 base pairs may, more preferably, be employed.

The target for the antisense nucleic acid may be anywhere within the genome, or transcribed RNA, so long as the antisense construct can be shown in vitro to inhibit expression of the targeted expression product and maintain its selectivity, and not seriously inhibit genes whose continued function is relied upon by the cell for normal cellular activities.

One can readily test whether the antisense nucleic acid is deleterious to the cell simply by testing the constructs in vitro to determine whether normal cellular function is affected or whether the expression of related genes having complementary sequences is affected.

In further aspects of the invention, antisense RNA can either be applied directly to cells, in the form of RNA oligonucleotides incorporating antisense sequences, or introduced into the cell as DNA encoding the desired antisense RNA.

In connection with these aspects of the invention, it is proposed that the antisense constructs of the present invention, whether they be antisense DNA molecules, antisense RNA molecules or DNA molecules which encode for antisense RNA molecules, will have their principal application in connection with the down-regulation of oncogene expression. By preparing a construct that encodes an RNA or DNA molecule that is in antisense or "complementary" configuration with respect to the RNA readouts or DNA of the target gene, the construct will act to inhibit or suppress the ultimate expression of the target gene, presumably by binding to the target RNA or DNA and thereby preventing its translation or transcription, respectively.

The most preferred oncogenes for application of the present invention will be those which specifically exist in hepatocytes or any other cell that expresses the CS protein receptor on its surface. One may mention, by way of example, oncogenes and oncogene families, such as ras, myc, neu, raf, erb, src, fms, jun and abl. Again, this list is not intended to be exhaustive but, rather, is exemplary of the more common oncogenes.

In further embodiments of the invention, with particular attention to liver cells, the antisense construct corresponds to a viral transcript, in particular an hepatitis viral transcript. In another preferred embodiment the antisense construct corresponds to a malaria transcript.

Targeted Ribozyme Construct Delivery

As an alternative to targeted antisense construct deliveriy, targeted ribozymes may be used. The term "ribozyme" is intended to refer to the targeting of oligonucleotides against complementary base sequences in DNA and RNA and their subsequent cleavage by the ribozyme. Ribozymes can either be applied directly to cells, in the form of RNA oligonucleotides incorporating ribozyme sequences, or introduced into the cell as DNA encoding the desired ribozyme RNA. Ribozymes may be used and applied in much the same way as described for antisense nucleic acids.

Pharmaceutical Compositions

Where clinical application of circumsporozoite region II-containing polypeptide/nucleic acid-binding agent is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the vector stable and allow for vector uptake by target cells.

Aqueous compositions of the present invention comprise an effective amount of the nucleic acid, such as a therapeutic gene, bound to the circumsporozoite region II-containing polypeptide/nucleic acid binding agent, dissolved or dispersed in a pharmaceutically acceptable carrier or aqueous medium. Such compositions can also be referred to as inocula. As mentioned above, therapeutic gene is intended to refer to any nucleic acid introduced into a cell for the potential benefit of the cell or the individual organism as a whole. This includes, among other things, as obvious to one skilled in the art, tumor suppressors, cytokines, antisense constructs and ribozymes.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalents and the like.

The active compounds also may be formulated for parenteral administration, e.g., formulated for injection via the intravenous, intramuscular, sub-cutaneous, hepatic or even intraperitoneal routes. The preparation of an aqueous composition that contains the therapeutic gene complex as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A therapeutic gene complexed to the circumsporozoite region II-containing polypeptide/nucleic acid-binding agent of the present invention, can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active peptide, peptides or agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Therapeutic Kit Components

Therapeutic kits comprising a circumsporozoite region II-containing polypeptide, nucleic acid binding agent, a nucleic acid of choice complexed together and an endosomal lysis agent, form another aspect of the invention. Such kits will generally contain, in suitable container means, pharmaceutically acceptable formulation of the complex comprising of circumsporozoite region II-containing polypeptide, nucleic acid agent, with or without the nucleic acid of choice, and pharmaceutically acceptable formulation of an endosomal lysis agent. The kit may have a single container means that contains circumsporozoite region II-containing polypeptide and nucleic acid agent with or without the nucleic acid of choice and the endosomal lysis agent or it may have distinct container means for each compound.

When the components of the kit are provided in one or more liquid solutions, the liquid solution is an aqueous solution, with a sterile aqueous solution being particularly preferred. The circumsporozoite region II-containing polypeptide/nucleic acid agent/nucleic acid complex and endosomal lysis agent may also be formulated into a syringeable composition. In which case, the container means may itself be a syringe, pipette, eye dropper, or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent also may be provided in another container means.

The container means generally will include at least one vial, test tube, flask, bottle, syringe or other container means, into which the circumsporozoite region II-containing polypeptide/nucleic acid agent/nucleic acid complex may be placed. The kit also will generally contain a second vial or other container into which the endosomal lysis agent may be placed. The kits also may comprise a second/third container means for containing a sterile, pharmaceutically acceptable buffer or other diluent.

The kits of the present invention also will typically include a means for containing the vials in close confinement for commercial sale, such as, e.g., injection or blow-molded plastic containers into which the desired vials are retained.

Irrespective of the number or type of containers, the kits of the invention also may comprise, or be packaged with, an instrument for assisting with the injection/administration or placement of the ultimate complex composition within the body of an animal. Such an instrument may be a syringe, pipette, forceps, measured spoon, eye dropper or any such medically approved delivery vehicle.

Targeted Nucleic Acid Delivery to a Cell

The liver is a particularly attractive target for gene therapy as it plays a critical role in intermediary metabolism and is the site of expression of many genetic diseases including cancer. The phrase "hepatic cell-associated pathologic condition" is intended to refer to any diseases or abnormalities affecting liver cells or tissues. Such conditions may include cancer, hepatitis, malaria, cystic fibrosis, familial hypercholesterolemia, phenylketonuria or hemophila.

Alternativley the phrase "pathologic condition" is intended to refer to any diseases or abnormalities affecting any cell or tissue, including those mentioned above.

To relieve any pathologic condition, whether hepatic cell-associated or not, the CS ligand/nucleic acid-binding agent complex must deliver nucleic acid to a cell. In order to do this, it must first contact the cell. The phrase "contact", as used herein, is intended to refer to the structural proximity of two or more molecules needed before functional interaction can occur. The structural proximity is therefore dependent on the properties of the two or more molecules.

In the present invention, functional interaction may be defined as the recognition of the complex by CS receptor on the cell surface and endosomal-mediated internalization of the complex into the cell. In order to contact the CS ligand/nucleic acid-binding agent complex and nucleic acid complex with a cell in vitro, it is a simple matter to add or admix the complex with the cells, as evidenced in Examples 2 through 5.

In the in vivo setting, contacting an hepatic cell could involve direct injection into the hepatic vasculature. Equally, it could involve the administration of the soluble CS complex into the blood stream where it may pass the fenestrations in the liver parenchyma to reach the hepatocytes. In order to pass the fenestrations in the liver parenchyma, the size of the complex must be <200 nm. The exact size of CS complexes used in the present studies was not determined, however, previous study of ASOR-polylysine-DNA complex prepared under similar procedures gave molecular size of 80–100 nm (Cristiano et al., 1993). Perales et al. (1994) have recently reported that by changing salt conditions, it is possible to modulate the sizes of galactosylated poly(L-lysine)/DNA complex (to about 10 nm). The formation of such small complexes was found to correlate with the prolonged expression of transgene in the livers of intact animals.

CS protein receptors have been found in many cultured cells but not in the tissues from which they are obtained (Examples 4 and 5, Rich et al., 1990). This shows that the CS ligand/nucleic acid-binding agent complex may be used for ex vivo gene therapy for pathologic conditions, other than those of the liver. Ex vivo gene therapy refers to the isolation of cells from an animal, the delivery of a therapeutic gene into the cells, in vitro, and then the return of the modified cells back into an animal.

Primary mammalian cell cultures may be prepared in various ways. A preferred method is described, herein (Example 2), for hepatocytes. However, many other cell cultures may be established from tissues/cells in a similar manner, exemplary examples include ovary, pancreas, muscle and intestines. In order for the cells to be kept viable while in vitro and contacting the cells with the CS ligand/nucleic acid binding agent/nucleic acid complex it is necessary to ensure that the cells maintain contact with the correct ratio of oxygen and carbon dioxide and nutrients but are protected from microbial contamination. Cell culture techniques are well documented and are disclosed herein, in Example 2 and by reference (Freshner, 1992).

Once the in vitro culture conditions have upregulated CS receptor expression on the cell surface, the invention may then deliver a therapeutic gene into the cells. Finally the cells may be reintroduced into the original animal, or administered into a distinct animal, in a pharmaceutically acceptable form by any of the means described above. Thus providing an ex vivo method of treating a mammal with a pathologic condition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of CS-Poly(L-lysine) Conjugate

A. Methods

1. Recombinant CS Proteins and Peptides

Bacterially derived-CS recombinant proteins CS27IVC-His6 (27–123[NANPNVDP]$_3$[NANP]$_{21}$300–411), CS27IC-His6(27–123[NANPNVDP]$_3$[NANP]$_1$300–411) containing *P. falciparum* CS sequences from the T4 isolate were prepared according to the procedure previously described (Takacs and Girard, 1991; Stuber et al., 1990). The recombinant plasmids were constructed by inserting the corresponding encoded DNA sequences into PDS56/RBSII vector. A synthetic oligonucleotide encoding hexahistidine was ligated to the 3' end of the CS genes to facilitate the recombinant protein purification by metal chelate affinity chromatography. The constructs were transformed into *E. coli* strain M15. Recombinant protein DHFR-CSF1-His6 (|DHFR|6–146) which contains a mouse dihydrofolate reductase (DHFR) cDNA linked to amino acid residues 6–146 of the CS sequence and the engineered hexahistidine was described previously (Stuber et al., 1990).

Peptide E35 (SEQ ID NO:2) (EWSPCSVTCGNGIQVRIKPGSAN) and A128 (SEQ ID NO:3)(GNEIEPGNNAYGSQSDTDASELT), both have 23 amino acid residues, were synthesized on a Vega Coupler 250C synthesizer using tert-butoxycarbonyl chemistry and deprotected as described previously (Kuo et al., 1992). The peptides were purified by high performance liquid chromatography. The amino acid composition of the synthesized peptides were confirmed by amino acid analysis.

2. Preparation of CS Conjugate

CS protein was conjugated to poly(L-lysine) (molecular mass=26.3 kDa, Sigma, St Louis, Mo.) by 1-ethyl-3-(3-dimethylaminopropyl)-carbodiimide (EDC, Sigma) according to the protocol described by Cristiano et al. (1993). Standard reaction mixture (1.5 ml) contained 1 ml of CS protein (in 100 mM 3-[N-morpholino]propanesulfonic acid (MOPS) buffer, pH 7.3) and 0.5 ml of poly(L-lysine) also in 100 mM MOPS, pH 7.3. EDC powder was then directly added to the mixture so that the final concentrations of CS protein, poly(L-lysine), and EDC were 94.3 µM, 141.05 µM, and 90.90 mM, respectively. This molar ratio is comparable to those used by other investigators in the preparation of ASOR conjugates (Wu and Wu, 1987; Cristiano et al., 1993).

Fluorescein isothiocyanate (FITC)-polylysine (3.72 mg) was dissolved in 100 mM MOPS, pH 7.3, and EDC was added to the sample to a final concentration of 90.90 mM to mimic the conditions for the preparation of the CS conjugate. The reaction mixture was incubated at 25° C. for 18 hours. The mixture was applied to a superose 6 column (16×30 cm) pre-equilibrated in HBS (150 mM NaCl, 20 mM Hepes, pH 7.3). The samples were eluted with the same buffer at the velocity of 0.17 ml/min. and collected in 1 ml-fractions. The chromatography was monitored by UV absorption at 280 nm. Protein concentrations in each fraction were determined by Bio-Rad protein assay system according to vendor's specifications (Richmond, Calif.), using immunoglobulin G (IgG) as reference. The amounts of conjugates used throughout this study were based on this protein determination unless otherwise indicated.

Conjugates were analyzed by acid-urea gel electrophoresis according to the procedure described by McKee et al. (1994). Transferrin, ASOR, and BSA (Sigma, St. Louis) conjugates were prepared by the same procedure.

B. Results

Figure 2A:
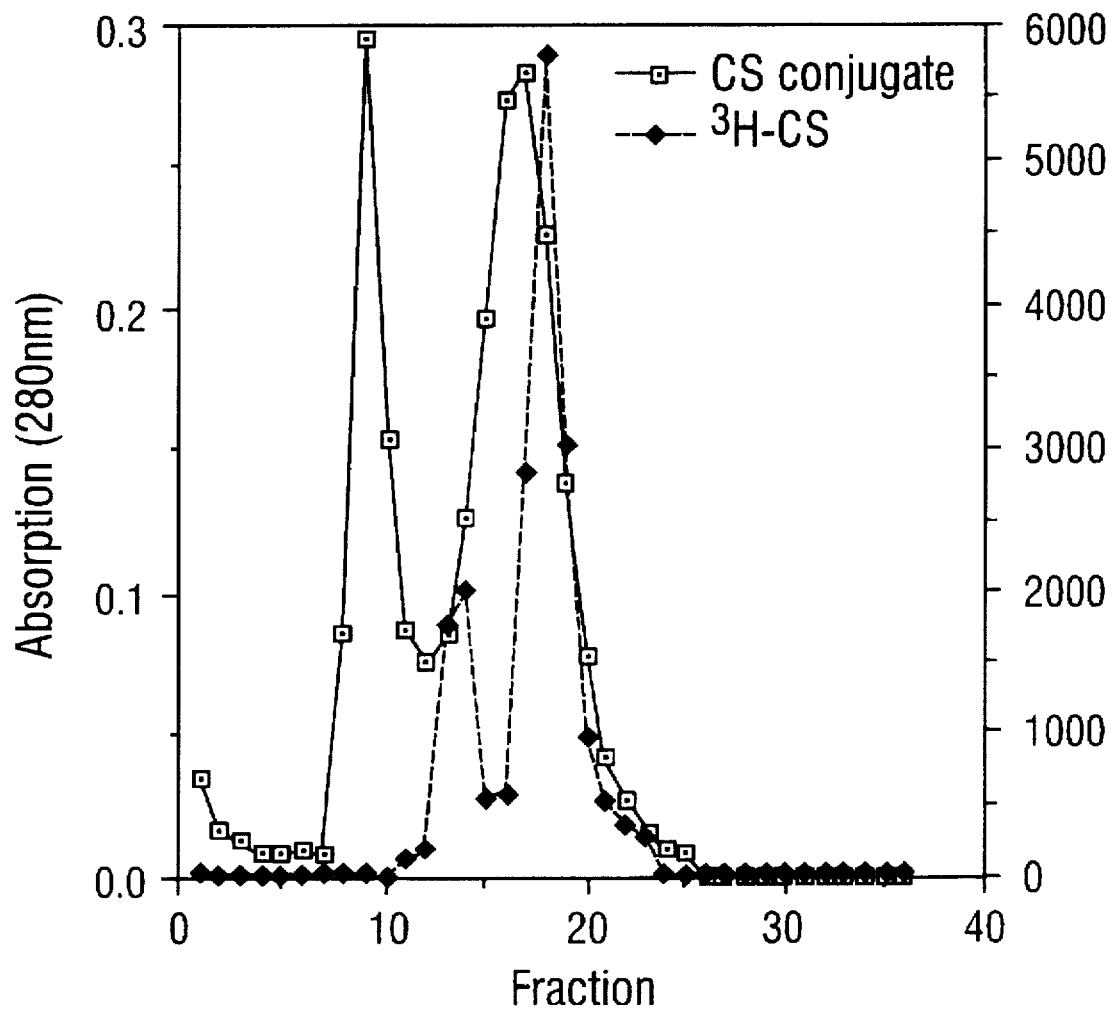

When $^3$H-recombinant CS27IVC-His6 protein (molecular mass=53 kDa, FIG. 1) was passed through a Superose 6 column and the eluents were monitored by radioactivity, two distinct peaks were resolved (FIG. 2A, dashed line). These two peaks may correspond to oligomeric (but predominantly dimeric) and monomeric CS proteins, respectively, since it has been reported that CS protein can oligomerized by cysteine formation (Cerami et al., 1992).

Figure 2B:
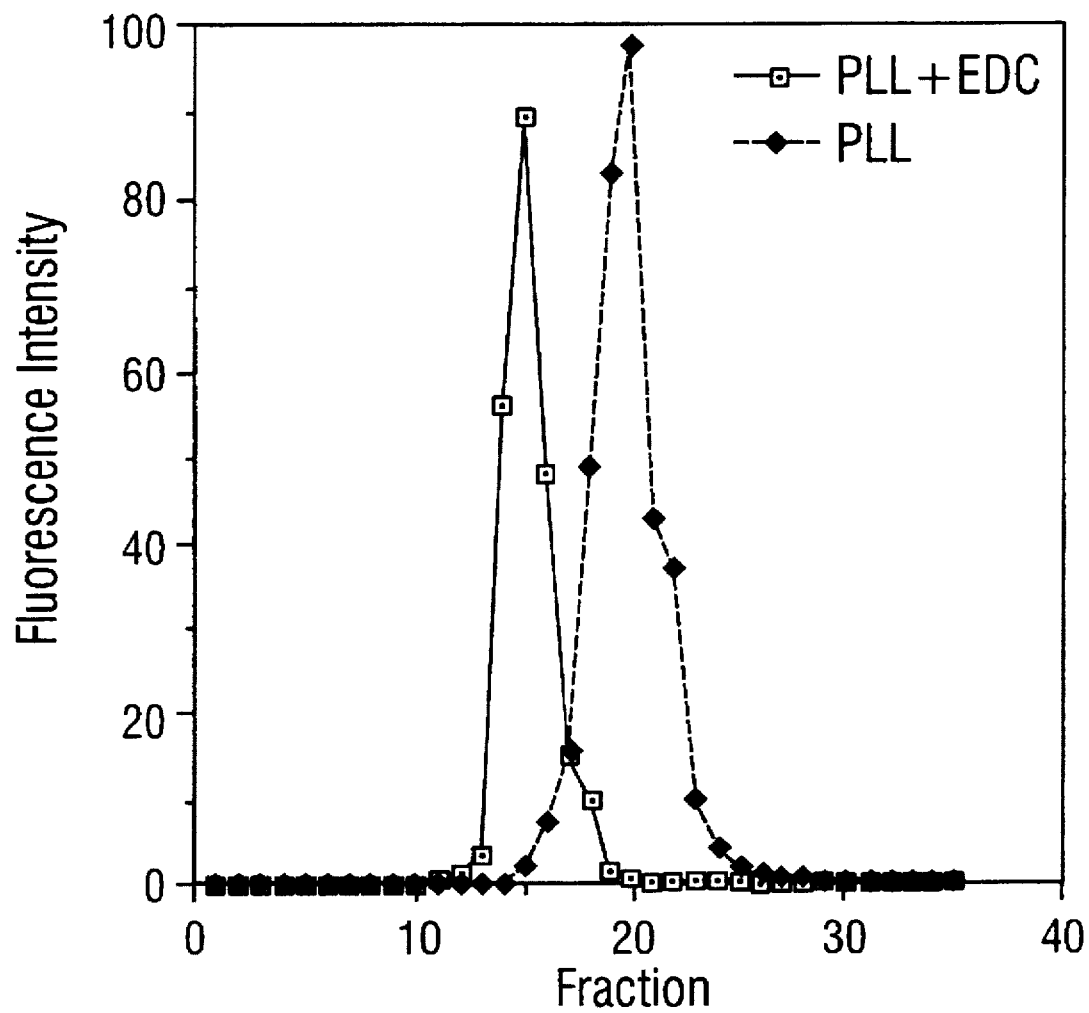
Figure 2C:
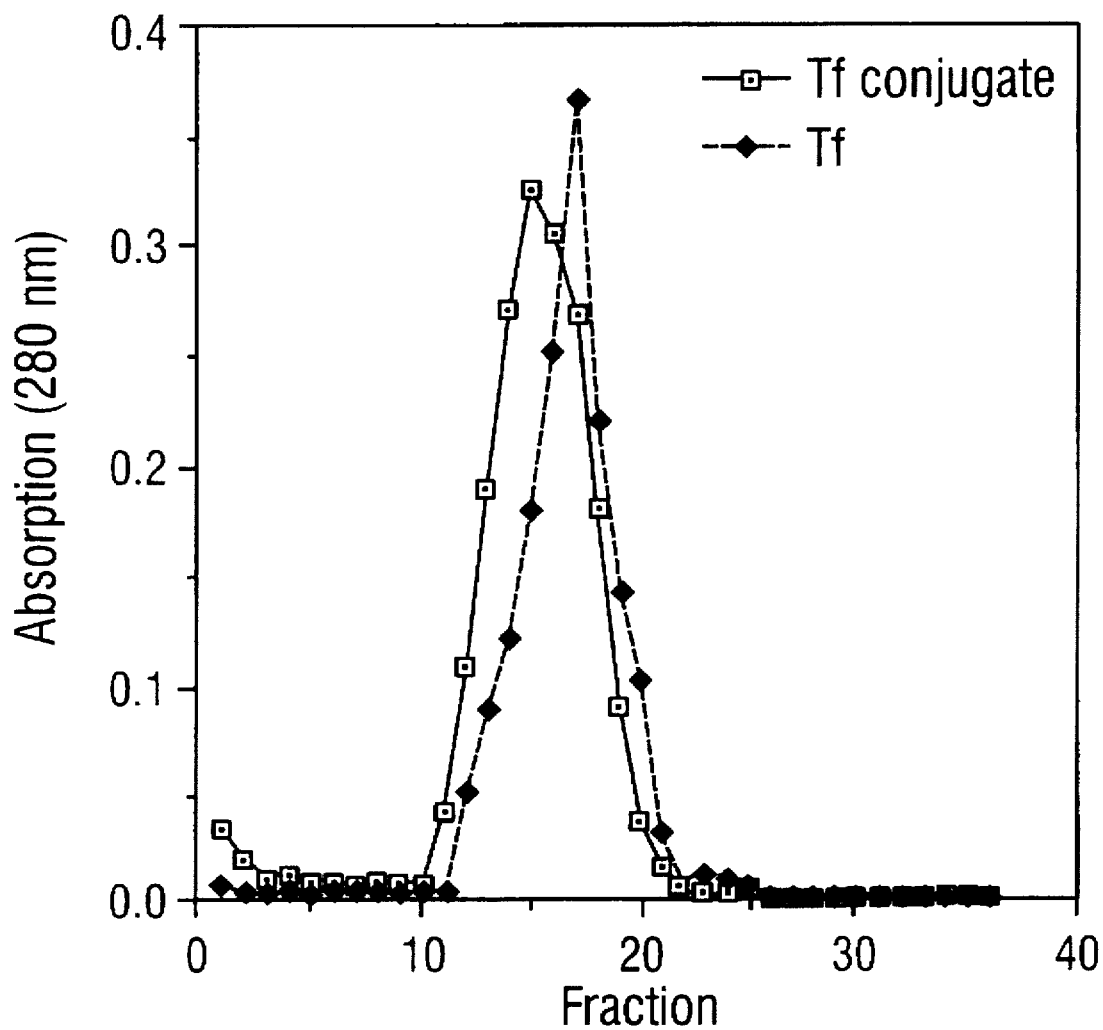

Recombinant CS27IVC-His$_6$ protein was conjugated to poly(L-lysine) (26.3 kDa) by EDC, and fractionated by the same column. Two distinct peaks were also eluted (FIG. 2A, solid line). The front peak had an apparent molecular mass of greater than 100 kDa, whereas the second peak, approx. 80 kDa, using the eluting profiles of presumptive multimeric CS protein (FIG. 2A) and unconjugated transferrin (80 kDa) (FIG. 2C, broken line) as references. These results suggested that the front peak contained CS conjugate with very little contamination of free CS protein.

When poly(L-lysine) alone was treated with EDC and fractionated through the same column, there was a shift in the eluting profile as compared with that of the untreated sample (FIG. 2B), indicating the formation of polylysine-polylysine conjugates. However, both the conjugated polylysine and free polylysine were eluted behind the front peak of the CS conjugate (compare between FIG. 2A and FIG. 2B). These results suggest that the front peak in the CS conjugate preparation should contain only negligible amount of polylysine-polylysine conjugates. Thus, these chromatographic conditions apparently are effective in the preparation of CS conjugates without significant contamination of free CS protein and self-conjugated polylysine. This is very important, because contamination would have an adverse effect on the efficacy of receptor-mediated gene delivery.

Figure 2D:
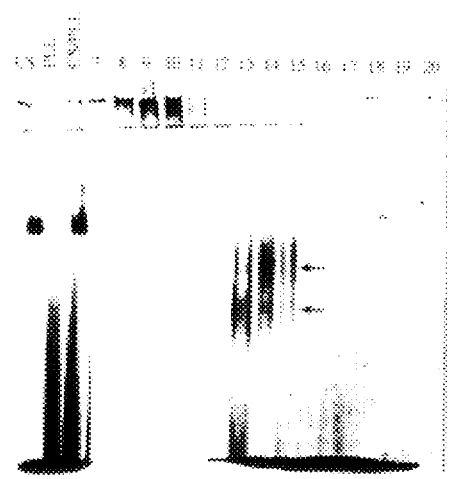

Aliquots from each fractions were determined by acid-urea polyacrylamide gel electrophoresis. Under these electrophoretic conditions, free polylysine and polylysine-polylysine conjugates more rapidly than did unconjugated CS protein and CS-polylysine conjugate (FIG. 2D), because of their high contents of positive charges. As shown in FIG. 2D, fractions eluted in the front peak (fractions 7–10) of the CS conjugate sample contained no detectable free polylysine; whereas, as expected, polylysine and/or polylysine-polylysine conjugates were only seen in the second peak (fractions 11–20).

Figure 2E:
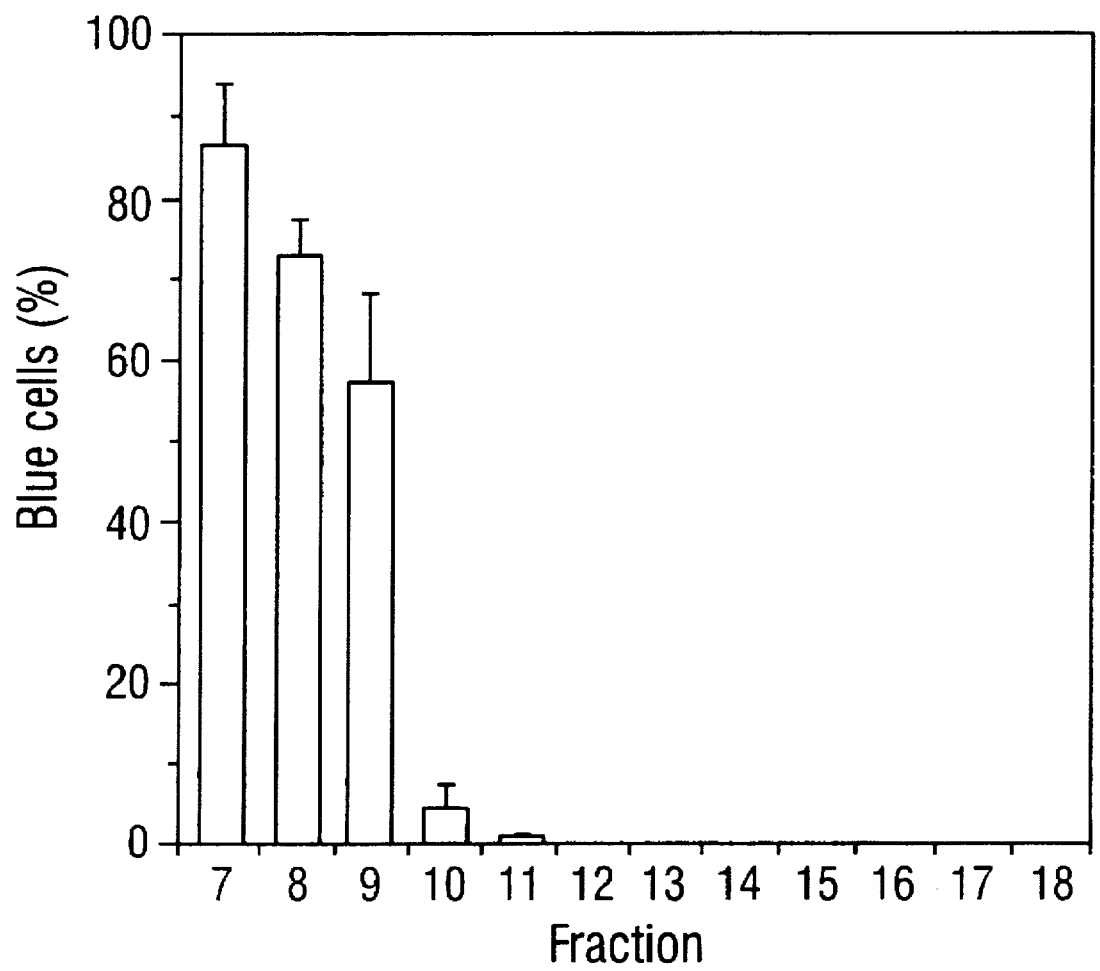
Figure 2F:
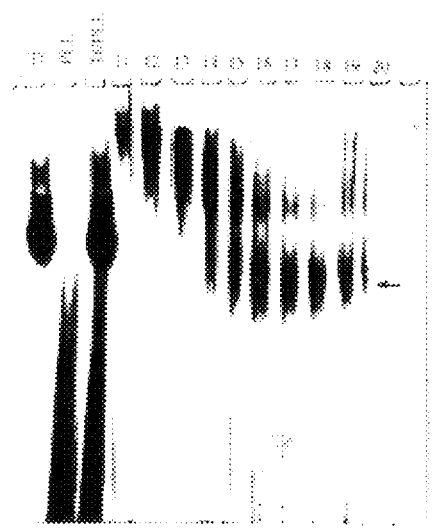
Figure 2G:
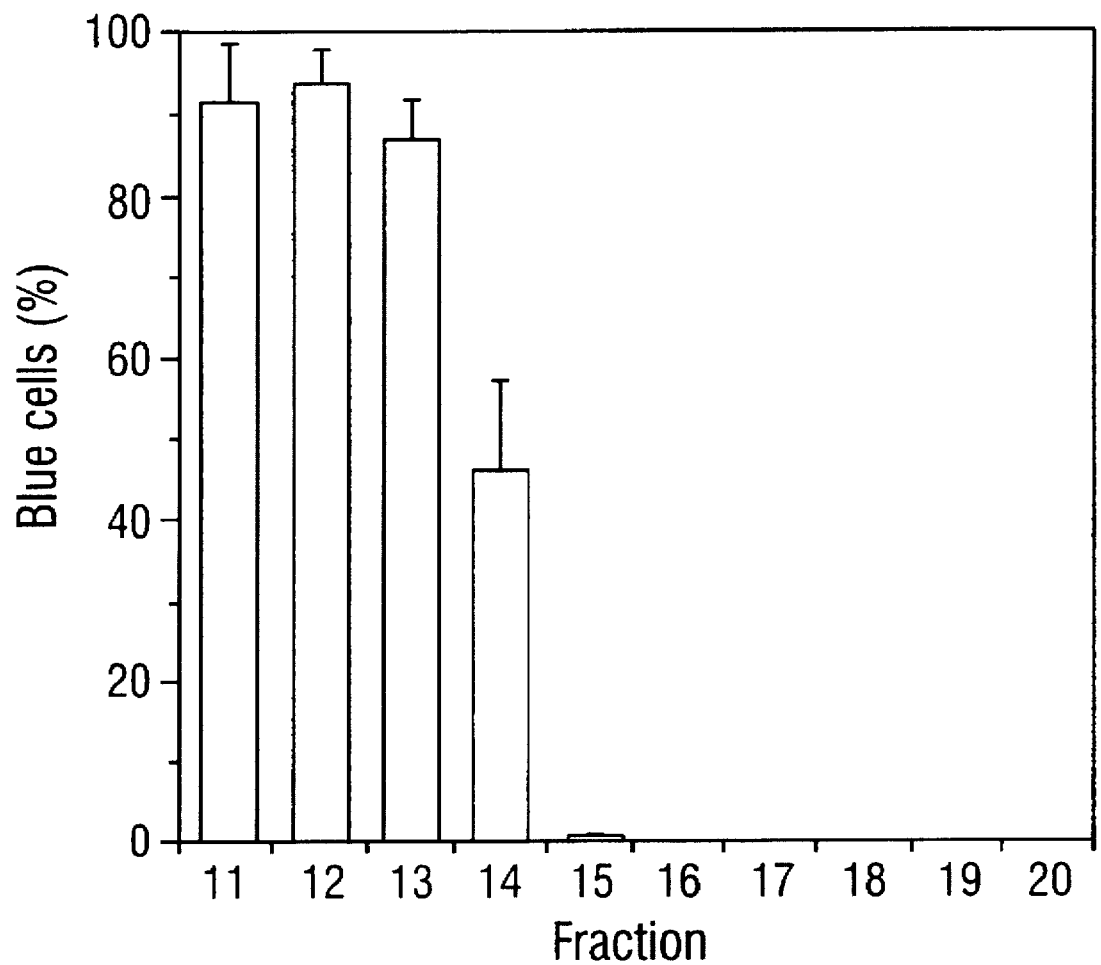

Proteins eluted in the front peak had a very slow mobility in this gel system, i.e., barely entering the stacking gel. These results suggest that the molecular size of these protein conjugates are rather large. The second peak also contained CS-polylysine conjugates, as suggested from their mobilities in the acid-urea gel electrophoresis (FIG. 2D, arrows). However, under the optimized transfection conditions (see below), only the conjugates from the front peak showed transfection activities (FIG. 2E).

The exact molecular mass of the conjugates in these two peaks have not been vigorously determined. The molar ratios of CS:polylysine in these types of conjugate preparations were not known. However, the results shown here were highly reproducible (five independent studies). Furthermore, similar results were obtained in the preparations of functional transferrin- (FIG. 2C, F, and G) and ASOR-poly-L-lysine conjugates. Thus, in conclusion, this simple gel filtration chromatographic technique can be used to prepare functional molecular carriers for gene delivery.

EXAMPLE 2

Optimization of Transfection Conditions for Primary Hepatocytes

A. Methods

1. Cells and Cell Culturing

Hepatocytes were isolated from adult male C57BL/6 mice by the procedure previously described (Kimura et al., 1994) with slight modification. Briefly, the livers were perfused with a solution containing collagenase (100 U/ml), trypsin inhibitor, 120 µg/ml (both from Worthington Biochem, Freehold, N.J.) and Hank A balance salts by cannulating the vena cava and releasing the perfusate via the portal vein. The resulting crude hepatocytes were suspended in 36% Percoll and further purified by centrifugation at 20,000×g for 20 min (Harbach et al., 1989). The purified hepatocytes usually had >95% viability at the time of plating as determined by trypan blue exclusion. The cells were suspended in Waymouth's MD 705/1 medium (GIBCO/BRL, Gaithersburg, Md.) containing 10% fetal calf serum (FCS) (GIBCO/BRL), penicillin (100 U per ml) and streptomycin (100 mg per ml) and plated onto Costar 6-well tissue culture plate 3506 at $3\times10^5$ cells/well.

CHO, HeLa, NIH3T3, and HepG2 cells were grown in Dulbecco's modified Eagle's medium (DMEM) supplemented with 10% FCS. HL-60 and K562 cells were maintained in RPMI 1640 medium containing 10% FCS. Cells were maintained in a 37° C. incubator containing 5% $CO_2$ in air.

2. Preparation of Adenovirus

Adenovirus dl312 was propagated in 293 cell and purified twice on CsCl density gradient according to the procedure described (Massie et al., 1986). The purified virus was dialyzed against HBS buffer (three times, one liter each). Viral DNA was extracted from aliquots of viral preparation by 1 hr SDS (0.1%) and proteinase K (100 µg/ml) digestion, followed by phenol/chloroform extraction and ethanol precipitation. The yield of DNA was spectrophotometrically determined at 260 nm absorbance, and used for calculation of the number of viral particles (Cristiano et al., 1993). The viruses were then aliquoted, and stored in HBS containing 10% glycerol at −80° C. until use. Recombinant adenoviruses harboring β-galactosidase linked to the cytomegalovirus promoter (Zhang et al., 1993) were prepared by the same procedure.

3. Formation of DNA Complex and Transfection

The reporter construct, pCMV-β-gal (MacGregor and Caskey, 1989), which contains a bacterial β-galactosidase gene under the transcriptional control of cytomegalovirus enhancer/promoter was used for transfection assay. Plasmid DNA was prepared by two times CsCl gradient ultracentrifugation. Six µg of pCMV-β-gal DNA in 350 µl HBS was mixed with various amounts of CS protein conjugate in 150 µl HBS. The mixture was incubated at 25° C. for 30 min. Before transfection, culture medium was removed and replaced by 0.5 ml of the medium containing 2% FCS. CS protein conjugate-DNA complex was added to the cells, immediately followed by addition of an appropriate amount of adenovirus. The cells were incubated at 37° C. for 2 hr. After addition of 2 ml of complete medium supplemented with 10% FCS, cells were incubated for an additional 16 hr.

4. β-galactosidase Activity Assay

β-galactosidase activity was analyzed by the methods described by MacGregor et al. (MacGregor et al., 1989). Briefly, The medium was removed from transfected cells. The cells were washed three times with PBS. The expression of β-galactosidase were determined either by histochemical staining (X-gal stains) or by measuring the enzymatic activity of cell extracts using ONPG as substrate. The unit of ONPG assay was defined as described by MacGregor et al. (MacGregor et al., 1989).

B. Results

To test whether the CS-polylysine conjugates could deliver recombinant DNA into primary hepatocytes, a set of pilot studies were carried out. CS27IVC-His6 protein conjugates from the front peak were complexed with recombinant pCMV-β-gal DNA. The DNA complexes were used to transfect primary hepatocyte cultures. Eighteen hours after transfection, cells were stained with X-gal. Less than 0.1% of positive cells were found. It is possible that the DNA complexes were internalized but not able to escape from endosomal entrapment.

Previous studies of ASOR and transferrin carriers demonstrated that adenovirus infection could destabilize endosomes, presumably allowing endosomally contained plasmid DNA to escape (Cristiano et al., 1993; Curiel et al., 1992; Wu et al., 1994; Curiel et al., 1991). Therefore, hepatocytes were cotransfected with a replication defective adenovirus (dl312).

The application of adenovirus greatly enhanced the frequency of X-gal positive cells, indicating that the efficiency of CS-mediated gene transfer also required endosomal destabilizing agents. Protein conjugates from the fractions of second peak were similarly analyzed, however, no more than 20% of blue cells were seen under various "optimization" conditions (see below). Thus, all the data presented here were using CS27IVC-His6 conjugates collected from the front peak of the Sepherose column (for simplicity, hereafter referred to as CS conjugate unless other specifications).

To demonstrate that the CS-mediated DNA transfection seen in the cultured primary hepatocytes was ligand-dependent and to optimize conditions for the transfection efficiency. Two parameters were investigated: CS conjugate to DNA ratio and the concentration of adenovirus. Six µg of reporter DNA were complexed with various amounts of CS conjugate. Hepatocyte cultures were transfected with these complexes. FIG. 3 shows that a maximal transfection efficiency of about 80% was achieved when 0.14 nM of CS conjugate was used, corresponding to a CS conjugate:DNA ration of 116:1. This optimal ratio of CS conjugate to DNA was comparable with those published using transferrin (Wagner et al., 1990) and ASOR (Cristiano et al., 1993) conjugates. In contrast, within the same ranges of carrier:DNA rations, BSA conjugates prepared under the same conditions showed no better than 10% of transfection efficiency. Likewise, less than 5% of transfection efficiency was seen with polylysine as a carrier. These results suggested that the transfection efficiency seen in the CS carrier is ligand-dependent.

It was important to investigate whether conjugates prepared by variations of ligand:polylysine:EDC ratio would affect the biological activities. To this end, conjugation reactions with fixed concentration of CS protein with increased concentrations of polylysine were carried out. To derive the reactions to completion because of increased polylysine, EDC concentrations were increased proportionally. Table 2 showed that conjugates prepared at the 1:1 to 1:2.5 molar ratios of CS protein:polylysine, greater than 80% of transfection efficiencies were achieved. However, the transfection efficiency was drastically reduced at molar ratio 1:5.0. The reason of this reduced transfection efficiency could be due to overmodification of the CS protein with polylysine, thereby reducing the accessibility of targetable ligand in the DNA.conjugate complexes.

TABLE 2

Optimization of CS:polylysine ratio during the preparation of CS conjugate

| Conjugation reaction | | | | Optimal | DNA: |
|---|---|---|---|---|---|
| CS27IC (µM) | Polylysine (µM) | CS:PLL ratio | EDC (mM)* | transfection efficiency (%)** | conjugate ratio |
| 58.80 | 58.80 | 1:1.0 | 37.79 | 83.26 ± 2.18 | 1:224 |
| 58.80 | 88.20 | 1:1.5 | 56.69 | 85.38 ± 0.78 | 1:116 |
| 58.80 | 147.00 | 1:2.5 | 94.49 | 80.12 ± 1.36 | 1:550 |
| 58.80 | 294.00 | 1:5.0 | 188.98 | 12.18 ± 2.78 | 1:80 |

*The amount of EDC was proportionally increase according to the polylysine concentration, i.e., always kept at 643 folds excess.
**Transfection was carried out with 6 µg of pCMV-β-gal DNA in the presence of adenovirus (4 × $10^4$ particles/cell). Transfection efficiency was determined by X-gal staining, and the blue cels rate was determined by counting 800-1000 cells from 3 different fields in duplicated samples.

To determine the optimal viral concentration for transfection, conjugate:DNA complex at a ratio of 116 to 1 was added to primary hepatocyte cultures followed by addition of different amounts of virus particles. As shown in FIG. 4, increasing adenovirus particles resulted in increased transfection efficiency with optimal amount of viral concentration of $4 \times 10^4$ particles/cell under the transfection conditions. Additional viral particles resulted in decreased transfection efficiency, probably due to excess cytotoxicity of viral infection. The viabilities of transfected cells decreased as the viral concentrations increased.

Under the optimal transfection conditions, about 58% of cells were viable (or 66% after correcting against the plating efficiency which was about 90%). Since substantial cell death was found at the optimal adenovirus concentration of CS-mediated gene transfer, it was of importance to investigate whether there is a causal relationship between adenovirus-induced cytotoxicity and the reporter gene expression. To this end, the following kinetics study was performed.

Primary hepatocytes in cultures were transfected with CS conjugate/DNA complex in the presence of adenovirus. At different time intervals, the cultures were terminated and expression of reporter gene and cell viability were determined. As shown in FIG. 5, expression of β-galactosidase appeared six hours after transfection, reached its maximum around 15 hrs, and decreased thereafter. On the other hand, cell viability decreased as the transfection time increased in a linear pattern. At the time when the reporter gene started to express (six hours after transfection), 80% of cells were still viable, while at the maximal levels of expression, 60%. Virtually no viable cells were detected after 48 hr transfection. These results suggest that the use of adenovirus as an enhancer for reporter gene expression in receptor-mediated gene delivery caused important toxicity.

EXAMPLE 3

Dependence of CS Protein-Mediated Gene Delivery upon the Evolutionarily Conserved Region II+ Epitope To investigate the functional domain in CS protein for mediating the DNA transfer, recombinant constructs containing deletions in various regions of the CS protein (FIG. 1) were tested. Recombinant CS27IC-$His_6$ which contains regions I and II+ but only one copy of the NANP repeat (instead of the 21 copies as in CS27IVC-$His_6$), had 84% transfection efficiency in the primary hepatocyte cultures (Table 3). This transfection efficiency was consistent with that using the CS27IVC-$His_6$ conjugates. However, recombinant DHFR-CSF1 (FIG. 1) which lacks region II+ and the entire NANP repeats, but retains only region I, showed poor gene transfer ability (Table 3). Histochemical staining of the transfected cells using these various conjugates are shown in FIG. 6. These results suggest that region II+ is important for CS-mediated gene delivery.

TABLE 3

Transfection efficiency of different CS conjugates

| Conjugate | Blue cells (%) |
|---|---|
| a. β-CMV DNA | <0.1 |
| b. CS 27IVC conjugate | 80.20 ± 5.24 |
| c. CS 27IC conjugate | 84.16 ± 8.32 |
| d. DHFR-CSF1 conjugate | <1.00 |

To confirm the importance of region II+ in CS-mediated gene delivery, a peptide containing region II+ sequence of CS protein (E35, SEQ ID NO:2) was used as a competitor for the CS-mediated gene transfer. Different amounts of E35 peptide, ranging from 0.031 μM to 0.248 μM, were added to the transfection mixture. The efficiencies of transfection were analyzed in comparison with those using an unrelated peptide (A128, SEQ ID NO:3) with different sequence but the same length as competitor. In the presence of 0.125 μM E35 peptide, greater than 50% of β-galactosidase activity was inhibited and the activity was completely ablated when 0.248 μM of E35 was added. However, at the comparative concentrations, peptide A128 showed no competitive effect (FIG. 7). These results further supported the notion that region II+ of CS protein contains functional residues for gene transfer.

These observations have important implications in the use of CS protein as a liver-specific gene targeting carrier. These repeats are immunodominant and confer the major antigenicity of CS protein. Human sera from *P. falciparum* malaria parasite-infected individuals in endemic areas contained mainly antibodies against the CS repeats (Nussenzwig and Nussenzwig, 1989; Miller et al., 1994). On the other hand, antibody against region II+ has not been detected in the human sera of malaria-infected individuals. Moreover, antibodies to region II have been difficult to elicit by immunization of mice and rabbits (Ballou et al., 1985). The fact that deleting the immunodominant domain did not compromise the ability of gene transfer (Table 3) suggests that repeat-free CS protein can be used as a ligand for gene delivery with reduced immunogenic complications to the hosts.

Region II+ is the epitope for receptor binding (Nussenzwig and Nussenzwig, 1989). It contains evolutionarily conserved amino acid residues with homology to cell adhesive motif found in several other proteins, including thrombospondin (Robson et al., 1988), properdin (Goundis and Reid, 1988), and a blood-stage antigen of *P. falciparum* (Goundis and Reid, 1988). The fact that region II+ peptide can block the CS-mediated gene transfer (FIG. 7) shows that the synthetic peptide containing region II+ residues can be used as a ligand for gene targeting via CS receptor.

EXAMPLE 4

Dependence of CS Protein-Mediated Gene Delivery Upon its Receptors

A. Methods

1. Uptakes of CS27IVC-His6 and Conjugate-DNA Complex

CS27IVC-His6 was tritium-labeled by sodium cyanoboro [$^3$H]hydride according to the procedure previously described (Mean, 1977). Briefly, one milligram of CS protein in 1 ml of HBS was added to 10 mCi sodium cyanoboro [$^3$H]hydride in the presence of 12 mM formaldehyde. The reaction was proceeded at 4° C. for 30 min. Labeled CS protein was purified by sephadex G-25 chromatography. The specific activity of labeled protein was 68,000 cpm/μg counted in a Beckman LS 3801 liquid scintillation counter.

Prior to protein uptake assay, the culture medium was replaced with 0.5 ml of serum-free medium. 2.5 μg of $^3$H-CS27IVC-His6 were added to the culture. The cells were incubated at 37° C. in 5% $CO_2$ incubator. At indicated time intervals, the medium was removed. The cells were wash three times with phosphate-buffered saline (PBS) and lysed with 0.5 ml of 0.5N NaOH. The radioactivity of cell lysate was counted in Scintiverse (Fisher) by a liquid scintillation counter (Beckman LS3801).

To determine uptake of CS conjugate/DNA complex, pCMV-β-gal plasmid DNA was nick-translated with $^{32}$P-dCTP using nick translation kit (GIBCO) according to the protocols provided by the vender. The labeled DNA was purified by Sephadex G25 chromatography. Ten ng of $^{32}$P-labeled DNA was mixed with 2.99 μg of unlabeled pCMV-β-gal DNA. The DNA was then mixed with 3.7 μg of CS conjugate in a total volume of 500 μl HBS. The formation of DNA complex was checked by gel retardation assay on a 0.8% agarose gel. The DNA complex was then diluted to 1 ml with serum-free medium and added to 5×10$^5$ primary hepatocytes or HL-60 cells. The cells were incubated at 37° C. in 5% $CO_2$ incubator. At different time intervals, the medium was removed and the radioactivities in the cultured cells were determined.

B. Results

Figure 8:
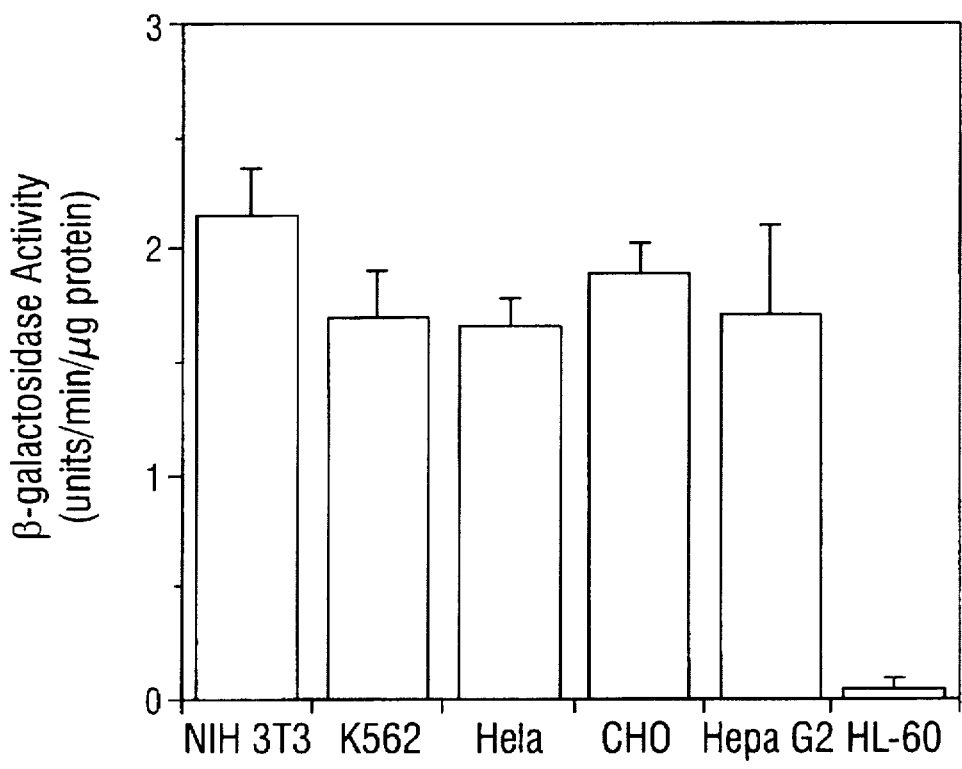

Although in vivo study has demonstrated that CS protein almost exclusively binds to hepatocytes, using a cell adhesion assay, Rich et al. (1990) implicated that CS receptors are present in a broad range of established cell lines, particularly CEM, HSB-2, K562, and KG-1 lymphocytic cell lines. Therefore, the inventors investigated whether the efficiency of CS-mediated gene transfer could be correlated with the presence of receptors on these various cell lines. HepG2 (Nussenzweig and Nussenzweig, 1989) and CHO (Frevert et al., 1993; Pancake) cells which have been reported to contain high levels of CS receptor, and HL-60 cells, that contain low levels of receptors (Rich et al., 1990) were chosen. pCMV-β-gal reporter gene was transfected into these cells using conjugates prepared from CS27IVC-His$_6$ protein. Under the optimal conditions, CHO and HepG2 cells exhibited 130 times higher β-gal activities than that of the HL-60 cells (FIG. 8).

The inability of CS protein-mediated gene transfer into HL-60 cells could be due to the absence of either adenovirus receptor or CS receptor, or both. To address the adenovirus receptor issue, HL-60 cells were transfected with recombinant β-gal adenovirus (ranging from 5×10$^6$ to 1×10$^9$ particles per 5×10$^5$ cells). It was found that this recombinant adenovirus has very poor transfection efficiency (<1% in HL-60 cells, in comparison of greater than 95% of transfection efficiency in HepaG2 cells. Although there may be other reasons for the inability of the expression of reporter gene in the adenovirus-infected HL-60 cells, the possibility of lacking adenovirus receptors in these cells could not be formally ruled out.

Figure 9:
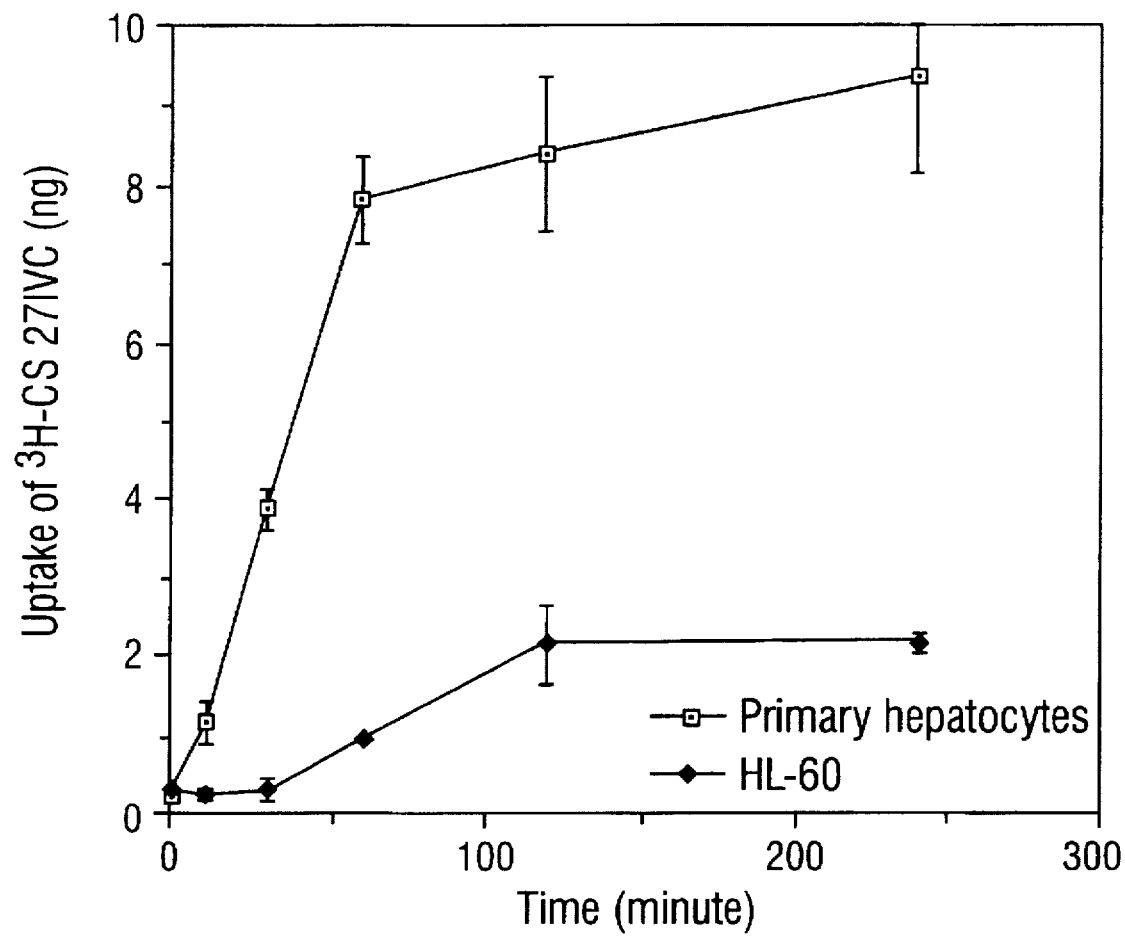

To address the issue of CS receptors in HL-60 cells, the rates of $^3$H-CS27IVC-His6 uptake in primary hepatocytes and in HL-60 cells were determined. Since it has been demonstrated that multimeric CS proteins were more efficiently uptaken then monomeric proteins by the liver parenchyma (Cerami et al., 1994), $^3$H-labeled multimeric CS fractions (the first peak, FIG. 2A, dash line) were used for the uptake study. As shown in FIG. 9, the levels of labeled CS protein uptake by HL-60 cells were significantly lower than those in the primary hepatocytes, suggesting that HL-60 cells containing reduced levels of CS receptors.

Figure 10A:
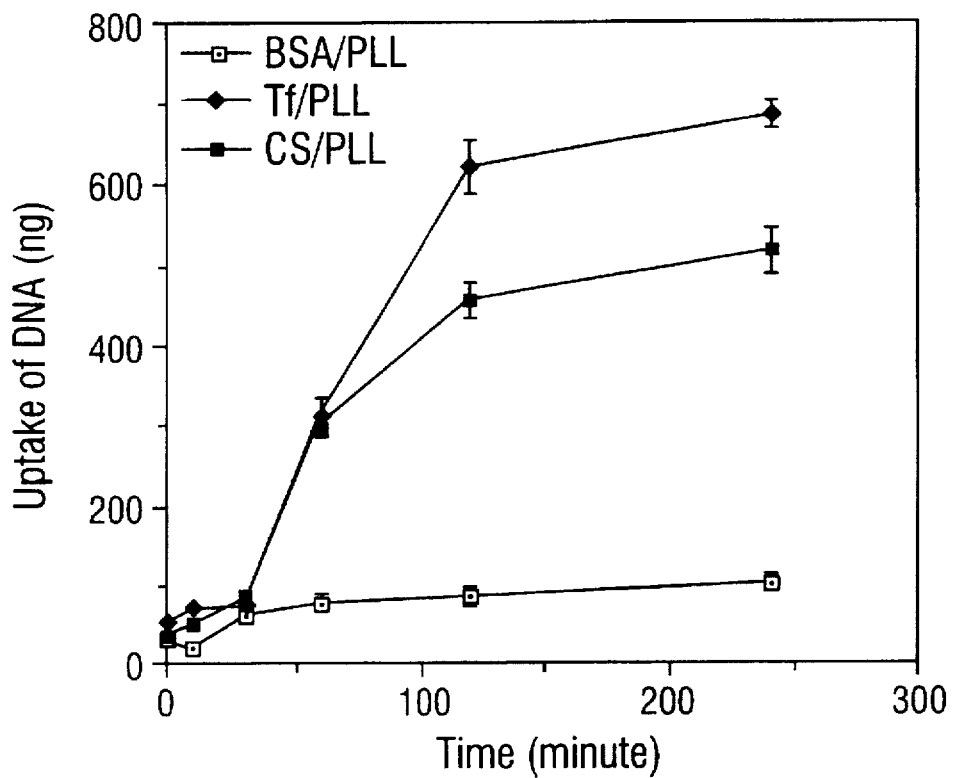
Figure 10B:
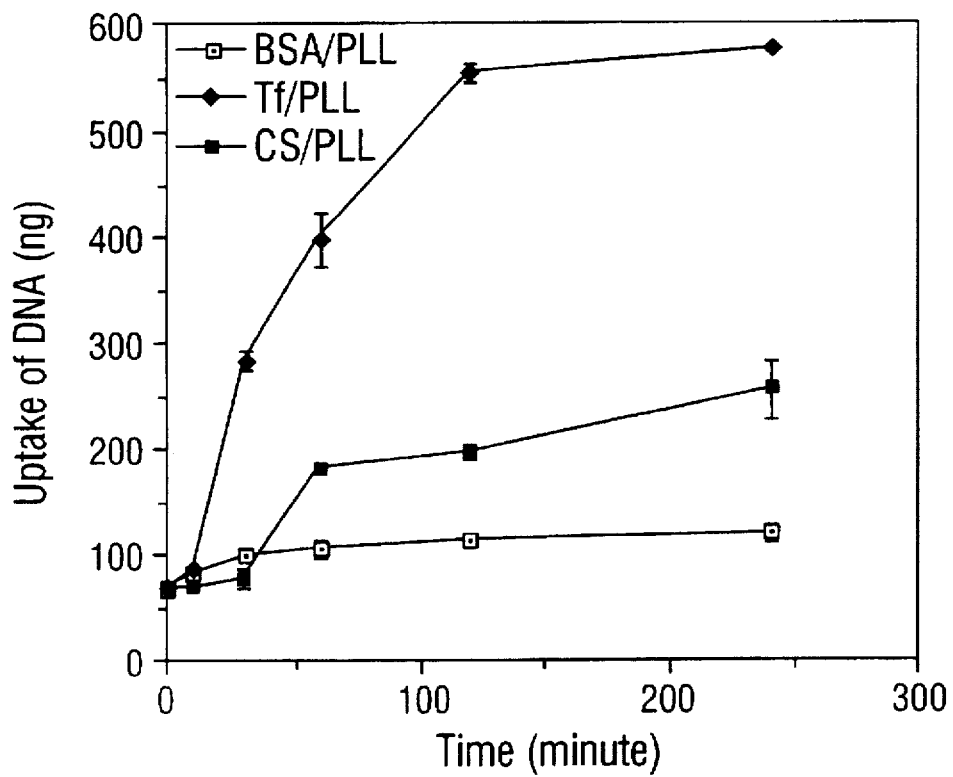
Figure 10A:
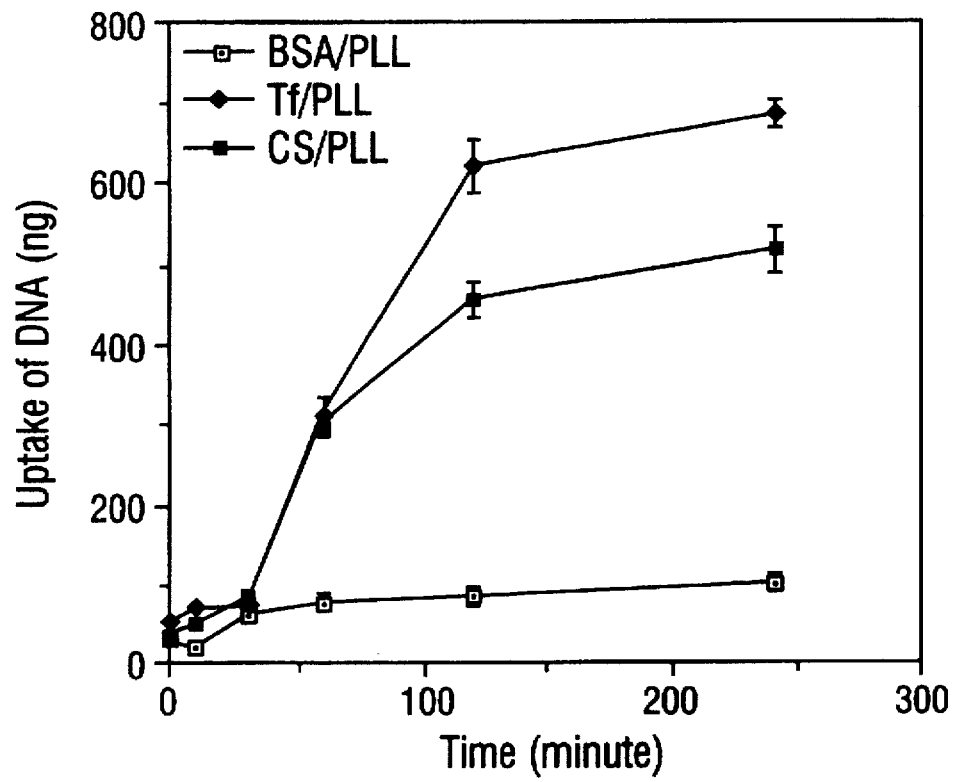
Figure 10B:
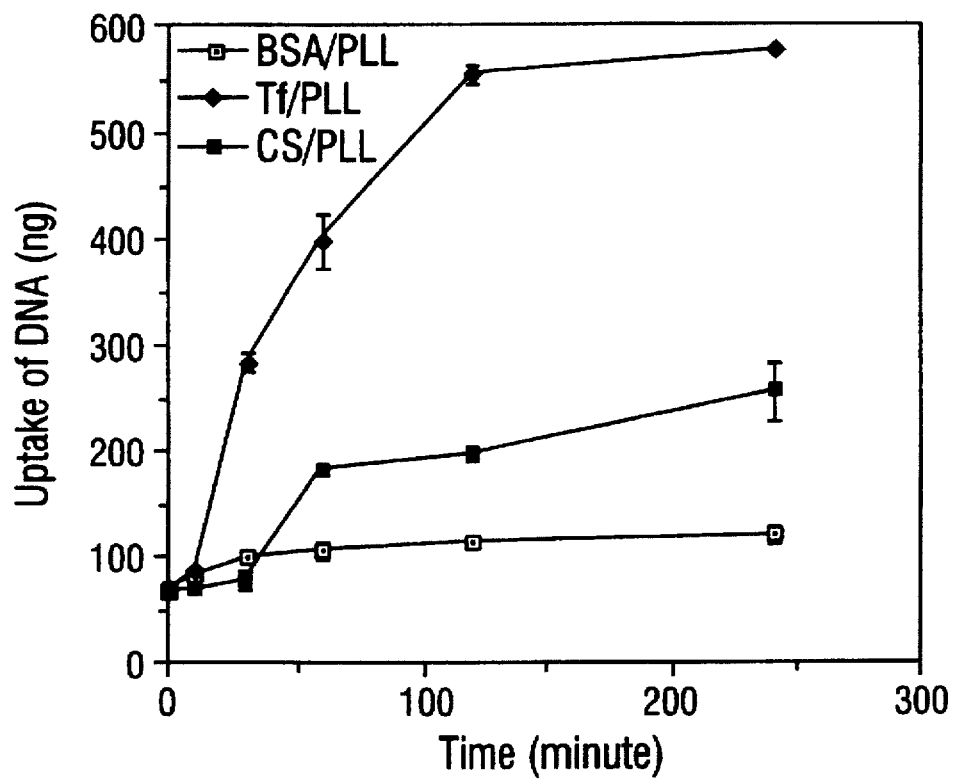

To substantiate these observations, the uptakes of DNA mediated by CS protein conjugates in these two different cell types were also measured, using transferrin-conjugates and BSA conjugates as positive and negative controls, respectively. As shown in FIG. 10A and FIG. 10B, the transferrin-DNA complexes were efficiently uptaken by both primary hepatocytes and HL-60 cells. However, the levels of CS-DNA uptake were significantly lower in HL-60 cells than those in primary hepatocytes. These results are consistent with the findings that the cell-type specificities of CS-mediated gene transfer are correlated with the presence of functional CS receptors.

Previous study has demonstrated that CS protein binds to heparan sulfate proteoglycans associated with the surface membrane of hepatocytes, and the binding can be abolished by heparinase treatment (Frevert et al., 1993; Pancake). These observations suggested that the CS receptor(s) may be heparan sulfate-related proteoglycans. In an attempt to determine whether the CS-mediated gene transfer into primary hepatocytes could be blocked by heparin and dextran sulfate (by competing CS-conjugate binding to receptors), however, it was found that these chemical causes dissociation of DNA from the CS conjugate, as judged by gel-retardation assay.

EXAMPLE 5

Gene Delivery by CS Conjugates in Various Cultured Cells

Since CS receptor has been found broadly distributed in established cell lines (Rich et al., 1990), CS conjugate may be used as a conventional tool for DNA transfer in different cell lines. To explore this possibility, NIH3T3 (normal fibroblast cell line), HeLa (tumor cell line), and K562 (suspension culture) were chosen for transfection using CS conjugates. HeLa, NIH3T3, and K562 all showed high transfection efficacies (FIG. 8). However, a number of human melanoma cell lines (A-375, HT-144 and WM115), and freshly prepared human bone marrow cells (gifts of Dr. Albert Deiseroth, M.D. Anderson Cancer Center) showed very low levels of transfection efficiencies. Whether the poor transfection efficiencies in these cells were due to the lack of adenovirus and/or CS receptors have not been determined. Nonetheless, these results demonstrated the CS conjugate can be used as a gene delivery carrier in some cultured cells.

The ability of CS-complex to elicit gene transfer into many established cell lines, including HeLa, NIH3T3, CHO, HepG2, and K562 cells (FIG. 8), is believed not to be due to alteration of CS protein configuration by polylysine conjugation that resulted in changes in ligand specificity for the following reasons: (i) the transfection is ligand-dependent, very low transfection efficiency was seen using BSA conjugates or polylysine as carriers (FIG. 5); (ii) the transfection efficiencies in different cell types were correlated with the levels of cellular receptor(s). Very low transfection efficiency was found in HL-60 cells in which receptor levels were low (FIG. 9 and FIG. 10A and FIG. 10B). (iii) The transfection efficiencies were region II+-dependent, consistent with the binding specificity of CS protein to its receptor (Nussenzweig and Nussenzweig, 1989). These observations suggest a broad applicability of CS protein as gene delivery vehicle for cultured cells. In this regard, CS protein may also be utilized for gene transfer into patient-derived cell cultures in the ex vivo gene therapy.

In conclusion, the present study established that the CS protein can be an effective system for gene transfer into primary hepatocyte cultures as well as into many different cultured cell lines. The ability to introduce foreign genes into mammalian cells in vitro is an important procedure for studying gene regulation. In addition, the specificity and solubility of the invention are important aspects of therapy for genetic defects in vivo.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arima, T., Motoyama, Y., Yamamoto, T., Nagata, K., and Kondo, T. (1977) *Gastroenterol. JPN.* 12, 39–421.

Ballou, W. R., Rothbard, J., Wirtz, R. A., Gordon, D. M., Williams, J. S., Gore, R. W., Schneider I., Hollingdale, M. R., Beaudoin, R. L., Maloy, W. L., Miller L. H. and Hockmeyer, W. T. (1985) *Science* 228, 996–999.

Cerami, C., Frevert, U., Sinnis, P., Takacs, B., and Nussenzweig, V. (1994) *J. Exp. Med.* 179, 695–701.

Cerami, C., Frevert, U., Sinnis, P. Takacs, B., Clavijo, P., Santos, M. J. and Nussenzweig, V. (1992) *Cell* 70, 1021–1033.

Cotten, M., Wagner, E., Zatloukal, K., and Birnstiel, M. L. (1993) *J. Virol.* 67, 3777–3785.

Cotten, M., Wagner, E., Zatloukal, K., Phillips, S., Curiel, D. T., and Birnstiel, M. L. (1992) *Proc. Natl. Acad. Sci. USA* 89, 6094–6098.

Cox, F. E. G. (1992) *Nature* 359, 361–362.

Cristiano, R., Smith, L. C., and Woo, S. L. C. (1993) *Proc. Natl. Acad. Sci. USA*, 90, 2122–2126.

Cristiano, R. J., Smith, L. C., Kay, M. A., Brinkley, B. R., and Woo, S. L. C. (1993) *Proc. Natl. Acad Sci. USA*, 90, 11548–11552.

Crystal, R. G., McElvaney, N. G., Rosenfeld, M. A., Chu, C-S., Mastrangeli, A., Hay, J. G., Brody, S. L., Jaffe, H. A., Eissa, N. T., and Danel, C. (1994) *Nature Genet.*, 8, 42–51.

Curiel, D. T., Wagner, E., Cotten, M., Birnstiel, M. L., Agarwall, S., Li, C. M., Loechel, S., and Hu, P. C. (1992) *Human Gene Ther.*, 3,147–154.

Curiel, D. T., Agarwal, S., Wagner, E., and Cotten, M. (1991) *Proc. Natl. Acad Sci. USA*, 88, 8850–8854.

Dodeur, M., Durand, D., Dumont, J., Durand, G., Geger, J., and Agneray, J. (1982) *Eur. J. Biochem.*, 123, 383–387.

Ferkol, T., Lindberg, G. L., Chen, J., Perales, J. C., Crawford, D. R., Ratnoff, O. D., and Hanson, R. W. (1993) *FASEB J.* 7, 1081–1091.

Freshner, R. I. (1992) *Animal Cell Culture: a Practical Approach*, Second Edition, Oxford/New York, IRL Press, Oxford University Press.

Frevert, U., Sinnis, P., Cerami, C., Shreffler, W., Takacs, B., and Nussenzweig, V. (1993) *J. Exp. Med.* 177, 1287–1298.

Girlich, D., and Rapoport, T. A. (1993) *Cell* 75, 615–630.

Goundis, D., and Reid, K. B. M. (1988) *Nature* 335, 82–85.

Harbach, P. R., Aaron, C. S., Wiser, S. K., Grzegorczyk, C. R., and Smith, A. L. (1989) *Mut. Res.* 216, 101–110.

Jaffe, H. A., Danel, C., Longenecker, G., Metzger, M., Setoguchi, Y., Rosenfeld, M. A., Gant, T. W., Thorgeirsson, S. S., Stratford-Perricaudet, L. D., Perricaudet, M., Pavirani, A., Lecocq, J.-P., and Crystal, R. G. (1992) *Nature Genet.* 1, 372–378.

Kay, M. A. and Woo, S. L. (1994) *Trends in Genetics* 10, 253–257.

Kimura, O., Yamaguchi, Y., Gunning, K. B., Teeter, L. D., Husain, F. and Kuo, M. T. (1994) *Human Gene Therap.* 5, 845–852.

Kuo, M. T., Zhao, J-Y., Teeter, L. D., Ikeguchi, M., and Chisari, F. V. (1992) *Cell Growth Differ.* 3, 531–540.

Kyte, J., & Doolittle, (1982) *J. Molec. Biol.*, 157:105–132.

MacGregor, G. R., and Caskey, C. T. (1989) *Nucleic Acids Res.* 17, 2365.

MacGregor, G. R., Nolan, G. P., Fiering, S., Roederer, M., and Herzenberg, L. A. (1989) in *Methods in Molecular Biology* (Murray, E. J. and Walker, J. M. eds.) 7, 217–235, Humana Press Inc., Clifton, N.J.

Marshall, J. S., Williams, S., Jones, P., and Hepner, G. W. (1978) *J. Lab. Clin. Med.* 92, 30–37.

Marshall, J. S., Green, A. M., Pensky, J., Williams, S., Zinn, A., and Carlson, D. M. (1974) *J. Clin. Invest.* 54, 555–562.

Massie, B., Gluzman, Y., and Hassell, J. A. (1986) *Mol. Cell Biol.* 6, 2872–2883.

McKee, T. D., DeRome, M. E., Wu, G. Y., and Findeis, M. A. (1994) *Bioconjugate Chem.* 5, 306–311.

Means, G. E. (1977) *Methods Enzymol.* 47, 469–478.

Miller, L. H., Good, M. F., and Milon, G. (1994) *Science* 264, 1878–1883.

Morgan, R. A., and Anderson, W. F. (1993) *Ann. Rev. Biochm.* 62, 191–217.

Nussenzweig, V., and Nussenzweig, R. S. (1989) *Adv. Immunol.* 45, 283–334.

Nussenzwig, R. S., and Long, C. A. (1994) *Science* 265, 1381–1388.

Pancake, S., Holt, G. D., Mellouk, S., and Hoffman, S. J. *Cell Biol.* 117, 1351–1357.

Perales, J. C., Ferkol, T., Beegen, H., Ratnoff, O. D., and Hanson, R. W. (1994) *Proc. Natl. Acad. Sci. USA* 91, 4086–4090.

Plank, C., Oberhauser, B., Mechtler, K., Koch, C., and Wagner, E. (1994) *J. Biol Chem.* 269, 12918–12924.

Rich, K. A., George IV, F. W., Law, J. L., and Martin, W. J. (1990) *Science* 249, 1574–1577.

Robson, K. J. H., Hall, J. R. S., Jennings, M. W., Harris, T. J. R., Marsh, K., Newbold, C. I., Tate, V. E., and Weatherall, D. J. (1988) *Nature* 335, 79–82.

Rothman, J. E., and Orci, L. (1992) *Nature* 355, 409–415.

Schwarts, A. L., and Rup, D. (1983) *J. Biol. Chem.* 258, 11249–11255.

Spiess, M., and Lodish, H. F. (1985) *Proc. Natl. Acad. Sci. USA* 82, 6465–6469.

Stuber, D., Bannwarth, W., Pink, J. R. L., Meloen, R. H., and Matile, H. (1990) *Eur. J. Immunol.* 20, 819–824.

Takacs, B. J., and Girard, M. F. (1991) *J. Immunol. Meth.* 143, 231–240.

Wagner, E., Zenke, M., Cotten, M., Beug, H., and Birnstiel, M. L. (1990) *Proc. Natl. Acad Sci. USA* 87, 3410–3414.

Wagner, E., Zatloukal, K., Cotten, Kirlappos, H., Mechtler, K., Curiel, D. T., and Birnstiel, M. L. (1992) *Proc. Natl. Acad. Sci. USA* 89, 6099–6103.

Wagner E., Plank, C., Zatloukal, K., Cotten M., and Birnstiel, M. L. (1992) *Proc. Natl. Acad Sci. U.S.A.* 89, 7934–7938.

Wang et al. (1994), *J. Biol. Chem.* 269, 9137–9146.

Wilson, J. M., Grossman, M., Wu C. H., Chowdhury, N. R., Wu, G. Y., and Chowdhury, J. R. (1992) *J. Biol. Chem.* 267, 963–967.

Wu, G. Y., and Wu, C. H. (1993) *Adv. Drug Delivery Rev.* 12, 159–167.

Wu, G. Y., Wilson, J. M., Shalaby, F., Grossman, M., Shafritz, D. A., and Wu, C. H. (1991) *J. Biol. Chem.* 266, 14338–14342.

Wu, G. Y., and Wu, C. H. (1987) *J. Biol Chem.* 262, 4429–4432.

Wu, G. Y., Zhan, P., Zes, L., Rosenberg, A. R., and Wu, C. H. (1994) *J. Biol. Chem.* 269, 11542–11546.

Zhang, W.-W., Fang, X., Branch, C. D., French, B. A., and Roth, J. A. (1993) *BioTechniques* 15, 868–872.

---

What is claimed is:

1. A complex comprising:
   (i) a ligand comprising a circumsporozoite region II-containing polypeptide; and
   (ii) a nucleic acid-binding agent.

2. The complex of claim 1, wherein said polypeptide is selected from the group consisting of CS27IVC-His$_6$ (SEQ ID NO:4), CS27IC-His$_6$ (SEQ ID NO:5), SEQ ID NO: 1 and SEQ ID NO:2.

3. The complex of claim 2, wherein said polypeptide is CS27IVC-His$_6$ (SEQ ID NO:4).

4. The complex of claim 2, wherein said polypeptide is CS27IC-His$_6$ (SEQ ID NO:5).

5. The complex of claim 2, wherein said polypeptide is SEQ ID NO:1.

6. The complex of claim 2, wherein said polypeptide is SEQ ID NO:2.

7. The complex of claim 1, wherein said nucleic acid-binding agent is a polycationic moiety.

8. The complex of claim 7, wherein said nucleic acid-binding agent is polylysine.

9. The complex of claim 1, further comprising an endosomal lysis agent.

10. The complex of claim 9, wherein said endosomal lysis agent is an infectious, replication-deficient adenovirus.

11. The complex of claim 1, further comprising a nucleic acid encoding a gene.

12. The complex of claim 11, wherein said gene is a cDNA.

13. The complex of claim 11, wherein said nucleic acid further comprises a promoter that is active in a cell expressing a CS receptor and is operably linked to said gene.

14. The complex of claim 13, wherein said gene encodes a tumor suppressor.

15. The complex of claim 13, wherein said gene encodes a cystic fibrosis transmembrane conductance regulator (CFTR).

16. The complex of claim 13, wherein said gene encodes a low density lipoprotein receptor.

17. The complex of claim 13, wherein said gene encodes a phenylalanine hydroxylase.

18. The complex of claim 13, wherein said gene encodes blood clotting factor IX.

19. The complex of claim 11, further comprising a nucleic acid encoding an antisense construct.

20. The complex of claim 1, further comprising a nucleic acid encoding a ribozyme.

21. A composition comprising:
   (i) a complex comprising
      (a) a ligand comprising a circumsporozoite region II-containing peptide, (b) a nucleic acid-binding agent, and (c) a nucleic acid comprising a gene;

(ii) a pharmaceutically-acceptable carrier, diluent or excipient.

22. A kit comprising:

(i) a ligand comprising a circumsporozoite region II-containing polypeptide; and (ii) a nucleic acid-binding agent.

23. The kit of claim 22, further comprising a nucleic acid encoding a gene.

24. The kit of claim 22, wherein said ligand and said nucleic acid-binding agent are complexed.

25. The kit of claim 22, wherein said ligand, said nucleic acid-binding agent and said nucleic acid are complexed.

26. A method of delivering a gene to a cell in culture comprising the steps of:

(i) providing a complex for the delivery of a gene to a cell comprising (a) a ligand comprising a circumsporozoite region II-containing polypeptide, (b) a nucleic acid-binding agent, and (c) a nucleic acid comprising said gene; and (ii) contacting said complex with said cell.

27. The method of claim 26, wherein step (ii) further comprises contacting said cell with an endosomal lysis agent.

28. The method of claim 27, wherein said endosomal lysis agent is an infectious, replication-deficient adenovirus.

29. The method of claim 26, wherein said gene is a cDNA.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Glu Trp Ser Pro Cys Ser Val Thr Cys Gly Asn Gly Ile Gln Val Arg
 1               5                   10                  15

Ile Lys
```

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Glu Trp Ser Pro Cys Ser Val Thr Cys Gly Asn Gly Ile Gln Val Arg
 1               5                   10                  15

Ile Lys Pro Gly Ser Ala Asn
                20
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Gly Asn Glu Ile Glu Pro Gly Asn Asn Ala Tyr Gly Ser Gln Ser Asp
 1               5                   10                  15

Thr Asp Ala Ser Glu Leu Thr
                20
```

( 2 ) INFORMATION FOR SEQ ID NO:4:

( i ) SEQUENCE CHARACTERISTICS:
        ( A ) LENGTH: 126 amino acids
        ( B ) TYPE: amino acid
        ( C ) STRANDEDNESS:

(D) TOPOLOGY: linear (xi) SEQUENCE DESCRIPTION: SEQ ID NO:4:

```
Asn Ala Asn Pro Asn Val Asp Pro Asn Ala Asn Pro Asn Val Asp Pro
1               5                   10                  15
Asn Ala Asn Pro Asn Val Asp Pro Asn Ala Asn Pro Asn Ala Asn Pro
                20                  25                  30
Asn Ala Asn Pro Asn Ala Asn Pro Asn Ala Asn Pro Asn Ala Asn Pro
                35                  40                  45
Asn Ala Asn Pro Asn Ala Asn Pro Asn Ala Asn Pro Asn Ala Asn Pro
                50                  55                  60
Asn Ala Asn Pro Asn Ala Asn Pro Asn Ala Asn Pro Asn Ala Asn Pro
65                              70                  75              80
Asn Ala Asn Pro Asn Ala Asn Pro Asn Ala Asn Pro Asn Ala Asn Pro
                85                  90                  95
Asn Ala Asn Pro Asn Ala Asn Pro Asn Ala Asn Pro Glu Trp Ser Pro
                100                 105                 110
Cys Ser Val Thr Cys Gly Asn Gly Ile Gln Val Arg Ile Lys
            115                 120                 125
```

(2) INFORMATION FOR SEQ ID NO:5:

(i) SEQUENCE CHARACTERISTICS:
  (A) LENGTH: 46 amino acids
  (B) TYPE: amino acid
  (C) STRANDEDNESS:
  (D) TOPOLOGY: linear (xi) SEQUENCE DESCRIPTION: SEQ ID NO:5:

```
Asn Ala Asn Pro Asn Val Asp Pro Asn Ala Asn Pro Asn Val Asp Pro
1               5                   10                  15
Asn Ala Asn Pro Asn Val Asp Pro Asn Ala Asn Pro Glu Trp Ser Pro
                20                  25                  30
Cys Ser Val Thr Cys Gly Asn Gly Ile Gln Val Arg Ile Lys
            35                  40                  45
```